US006496730B1

(12) United States Patent
Kleckner et al.

(10) Patent No.: US 6,496,730 B1
(45) Date of Patent: Dec. 17, 2002

(54) MULTI-SITE CARDIAC PACING SYSTEM HAVING CONDITIONAL REFRACTORY PERIOD

(75) Inventors: Karen J. Kleckner, New Brighton; Carleen J. Juran, Shoreview; Robert A. Betzold, Fridley; Thomas C. Wendell, White Bear Lake; Charles G. Yerich, Shoreview, all of MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/439,244

(22) Filed: Nov. 12, 1999

Related U.S. Application Data

(60) Provisional application No. 60/114,090, filed on Dec. 29, 1998, and provisional application No. 60/145,860, filed on Jul. 28, 1999.

(51) Int. Cl.[7] ................................................ A61N 1/36

(52) U.S. Cl. ......................................................... 607/9

(58) Field of Search ................................. 607/9, 14, 25

(56) References Cited

U.S. PATENT DOCUMENTS

| 3,937,226 A | 2/1976 | Funke ................... 128/419 PG |
| 4,088,140 A | 5/1978 | Rockland et al. ...... 128/419 PG |
| 4,332,259 A | 6/1982 | McCorkle, Jr. .............. 128/786 |
| 4,354,497 A | 10/1982 | Kahn ...................... 128/419 D |
| 4,458,677 A | 7/1984 | McCorkle, Jr. ............. 128/786 |
| 4,548,203 A | 10/1985 | Tacker, Jr. et al. ....... 128/419 D |

(List continued on next page.)

FOREIGN PATENT DOCUMENTS

| DE | 196 15 159 | 10/1997 | .......... A61N/1/362 |
| WO | WO 99/29368 | 6/1999 | .......... A61N/1/372 |

OTHER PUBLICATIONS

Daubert et al., "Permanent Left Ventricular Pacing With Transvenous Leads Inserted Into The Coronary Veins", PACE(vol. 21, Part II, pp. 239–245, Jan. 1998).

(List continued on next page.)

Primary Examiner—Jeffrey R. Jastrzab
(74) Attorney, Agent, or Firm—Girma Wolde-Michael

(57) ABSTRACT

Multi-site cardiac pacing systems for providing pacing to multiple sites in a patient's heart, e.g., in a single heart chamber or in right and left heart chambers, while avoiding inappropriate responses to double sensing of an evoked depolarization conducted between the sites. A conditional refractory period and further post-event time periods, e.g. a conventional refractory period, are started upon a sense event or pacing pulse sensed at or delivered to a first pace/sense site. A sense event detected at another sense site that occurs during the conditional refractory period is characterized as a conditional refractory event, and it restarts shortened post-event time periods and terminates the conditional refractory period. The restarted post-event time periods are reduced in length by the elapsed time between the starting and termination of the conditional refractory period. The undue prolongation of the post-event period due to a sense event resulting from sensing of delayed propagation of a depolarization between the spaced apart pace/sense sites is avoided. However, the full length post-event time periods are restarted if a sense event is then detected during the previously restarted post-event time periods. Multi-site single heart chamber pacemaker and right and left heart chamber pacemaker embodiments of the invention are disclosed. In an atrial synchronous, bi-ventricular pacemaker embodiment, the undue prolongation of the post-event period due to a ventricular event sense event resulting from sensing of delayed propagation of a single ventricular depolarization between the left and right ventricles is avoided, and legitimate atrial sense event signals occurring thereafter are not characterized as refractory and are able to restart the AV delay.

38 Claims, 13 Drawing Sheets

U.S. PATENT DOCUMENTS

| | | |
|---|---|---|
| 4,928,688 A | 5/1990 | Mower .................. 128/419 PG |
| 5,123,412 A | 6/1992 | Betzold ........................ 607/17 |
| 5,174,289 A | 12/1992 | Cohen .................. 128/419 PG |
| 5,267,560 A | 12/1993 | Cohen ........................... 607/25 |
| 5,292,340 A | 3/1994 | Crosby et al. |
| 5,387,228 A | 2/1995 | Shelton ......................... 607/11 |
| 5,403,356 A | 4/1995 | Hill et al. ...................... 607/14 |
| 5,514,161 A | 5/1996 | Limousin ........................ 607/9 |
| 5,540,727 A | 7/1996 | Tockman et al. .............. 607/18 |
| 5,584,867 A | 12/1996 | Limousin et al. ............... 607/9 |
| 5,674,259 A | 10/1997 | Gray ............................ 607/20 |
| 5,720,768 A | 2/1998 | Verbove-Nelissen ........... 607/9 |
| 5,728,140 A | 3/1998 | Salo et al. ....................... 607/9 |
| 5,741,309 A | 4/1998 | Maares ........................... 607/9 |
| 5,792,203 A | 8/1998 | Schroeppel ................... 607/30 |
| 5,797,970 A | 8/1998 | Pouvreau ........................ 607/9 |
| 5,902,324 A | 5/1999 | Thompson et al. ............. 607/9 |

OTHER PUBLICATIONS

Cazeau et a., "Four Chamber Pacing in Dilated Cardiomyopathy", *PACE*(vol. 17, Part II, pp. 1974–1979, Nov. 1994).

Daubert et al., "Renewal of Permanent Left Atrial Pacing via the Coronary Sinus", *PACE*(vol. 15, Part II, NASPE Abstracts 255, p. 572, Apr. 1992).

Daubert et al., "Permanent Dual Atrium Pacing in Major Intra–atrial Conduction Blocks: A Four Years Experience", *PACE*(vol. 16, Part II, NASPE Abstract 141, p.885, Apr. 1993).

MULTI-SITE CARDIAC PACING SYSTEM HAVING CONDITIONAL REFRACTORY PERIOD

CROSS-REFERENCE TO RELATED APPLICATIONS

This patent application claims the benefit of U.S. Provisional Application No. 60/114090 filed Dec. 29, 1998 and No. 60/145860 filed Jul. 28, 1999.

Reference is hereby made to the following, commonly assigned, co-pending, U.S. Patent Applications which disclose common subject matter:
Ser. No.09/290,967 filed on Apr. 13, 1999 for DUAL-CHAMBER PACEMAKER WITH OPTIMIZED PVARP FOLLOWING A PVC filed in the names of R. Betzold et al.; Ser. No. 09/067,729 filed Apr. 28, 1998 for MULTIPLE CHANNEL, SEQUENTIAL, CARDIAC PACING SYSTEMS filed in the names of C. Struble et al.; Ser. No. 09/439,569 filed on even date herewith for CARDIAC PACING SYSTEM DELIVERING MULTI-SITE PACING IN A PREDETERMINED SEQUENCE TRIGGERED BY A SENSE EVENT in the names of C. Yerich et al.; Ser. No. 09/439,565 filed on even date herewith for BI-CHAMBER CARDIAC PACING SYSTEM EMPLOYING UNIPOLAR LEFT HEART CHAMBER LEAD IN COMBINATION WITH BIPOLAR RIGHT HEART CHAMBER LEAD in the names of B. Blow et al.; Ser. No. 09/439,078 filed on even date herewith for MULTI-SITE CARDIAC PACING SYSTEM HAVING TRIGGER PACE WINDOW in the names of C. Juran et al.; Ser. No. 09/439,568 filed on even date herewith for RECHARGE CIRCUITRY FOR MULTI-SITE STIMULATION OF BODY TISSUE filed in the names of B. Blow et al.; and Ser. No. 09/439,243 filed on even date herewith for AV SYNCHRONOUS CARDIAC PACING SYSTEM DELIVERING MULTI-SITE VENTRICULAR PACING TRIGGERED BY A VENTRICULAR SENSE EVENT DURING THE AV DELAY in the names of C. Yerich et al.

FIELD OF THE INVENTION

The present invention pertains to multi-site cardiac pacing systems for pacing first and second sites of a patient's heart, particularly right and left heart chambers, e.g., the right and left ventricles, and operable in selected pacing modes while avoiding inappropriate responses to double sensing of an evoked depolarization conducted between the sites.

BACKGROUND OF THE INVENTION

In diseased hearts having conduction defects and in congestive heart failure (CHF), cardiac depolarizations that naturally occur in one upper or lower heart chamber are not conducted in a timely fashion either within the heart chamber or to the other upper or lower heart chamber. In such cases, the right and left heart chambers do not contract in optimum synchrony with each other, and cardiac output suffers due to the conduction defects. In addition, spontaneous depolarizations of the left atrium or left ventricle occur at ectopic foci in these left heart chambers, and the natural activation sequence is grossly disturbed. In such cases, cardiac output deteriorates because the contractions of the right and left heart chambers are not synchronized sufficiently to eject blood therefrom. Furthermore, significant conduction disturbances between the right and left atria can result in left atrial flutter or fibrillation.

It has been proposed that various conduction disturbances involving both bradycardia and tachycardia of a heart chamber could benefit from pacing pulses applied at multiple electrode sites positioned in or about a single heart chamber or in the right and left heart chambers in synchrony with a depolarization which has been sensed at at least one of the electrode sites. It is believed that cardiac output can be significantly improved when left and right chamber synchrony is restored, particularly in patients suffering from dilated cardiomyopathy and CHF.

A number of proposals have been advanced for providing pacing therapies to alleviate these conditions and restore synchronous depolarization and contraction of a single heart chamber or right and left, upper and lower, heart chambers as described in detail in commonly assigned U.S. Pat. Nos. 5,403,356, 5,797,970 and 5,902,324 and in U.S. Pat. Nos. 5,720,768 and 5,792,203 all incorporated herein by reference. The proposals appearing in U.S. Pat. Nos. 3,937,226, 4,088,140, 4,548,203, 4,458,677, 4,332,259 are summarized in U.S. Pat. Nos. 4,928,688 and 5,674,259, all incorporated herein by reference. The advantages of providing sensing at pace/sense electrodes located in both the right and left heart chambers is addressed in the '688 and '259 patents, as well as in U.S. Pat. Nos. 4,354,497, 5,174,289, 5,267,560, 5,514,161, and 5,584,867, also all incorporated herein by reference.

The medical literature also discloses a number of approaches of providing bi-atrial and/or bi-ventricular pacing as set forth in: Daubert et al., "Permanent Dual Atrium Pacing in Major Intra-atrial Conduction Blocks: A Four Years Experience", *PACE* (Vol. 16, Part II, NASPE Abstract 141, p.885, April 1993); Daubert et al., "Permanent Left Ventricular Pacing With Transvenous Leads Inserted Into The Coronary Veins", *PACE* (Vol. 21, Part II, pp. 239–245, Jan. 1998); Cazeau et al., "Four Chamber Pacing in Dilated Cardiomyopathy", *PACE* (Vol. 17, Part II, pp. 1974–1979, November 1994); and Daubert et al., "Renewal of Permanent Left Atrial Pacing via the Coronary Sinus", *PACE* (Vol. 15, Part II, NASPE Abstract 255, p. 572, April 1992), all incorporated herein by reference.

Problems surface in implementing multi-site pacing in a single heart chamber or in right and left heart chamber pacing within the contexts of conventional timing and control systems for characterizing and responding to sense event signals generated by sense amplifiers coupled to spaced apart pace/sense electrodes. Inappropriate responses can be triggered by depolarizations conducted between the separated pace/sense electrode sites and sensed by sense amplifiers coupled to those pace/sense electrodes which upset the timing of delivery of subsequent pacing pulses. In right and left heart pacing systems, pacing and sensing problems arise when right-to-left or left-to-right conduction delays vary depending on right and left ventricle pace/sense electrode placement, transient conditions of the heart, and chronic CHF.

In modern cardiac pacemakers, it is common to define certain blanking and refractory periods commenced after delivery of a pacing pulse and sensing of a depolarization wave traversing the pace/sense electrode. The input terminals of the sense amplifier are effectively uncoupled from the pace/sense electrodes during the blanking periods following delivery of a pacing pulse. The blanking periods are shorter than refractory periods which are started after both sense events and delivery of pacing pulses.

Sense events detected by a sense amplifier following time-out of a blanking period and during timing out of its refractory periods are characterized as "refractory sense events", and sense events occurring after time-out of the refractory periods are characterized as "non-refractory sense events". Non-refractory sense events trigger restarting pacing escape intervals or the AV delay in AV synchronous pacemakers. Refractory sense events restart various post-event time periods including refractory periods as described further below to avoid inappropriate tracking of repetitive noise signals that are mistakenly detected as sense events.

A delivered pacing pulse "captures" the heart if its delivery to a pace/sense electrode causes or "evokes" a myocardial contraction and depolarization wave that is conducted away from that pace/sense electrode site. The depolarization wave and accompanying contraction can be delayed in diseased hearts such that the depolarization wave can be sensed by a sense amplifier coupled to another pace/sense electrode at another site spaced from the paced pace/sense electrode site. The evoked depolarization wave can reach the non-paced pace/sense electrodes after time-out of the post-pace blanking period of the sense amplifier and be sensed during a post-event time period, e.g., a refractory period and be mistakenly characterized as a refractory sense event. The delayed sensing in one or the other of the paced sites can also occur if the pacing pulse delivered at that site fails to capture the heart. The mistakenly characterized refractory sense event restarts post-event blanking and refractory periods. The restarting of these post-event time periods can interfere with the sensing or proper characterization of subsequent true spontaneous depolarizations and disrupt delivery of pacing pulses.

In bi-chamber (bi-atrial or bi-ventricular) pacemakers, pacing pulses are delivered to one or the other or both of the right and left heart chambers upon expiration of a pacing escape interval. The escape interval is restarted upon delivery of a pacing pulse or upon a non-refractory sense event. Post-event time periods are started upon delivery of a pacing pulse or upon a refractory or non-refractory sense event. The delayed right-to-left or left-to-right conduction of an evoked depolarization resulting from delivery of a pacing pulse to the right or left heart chamber, respectively, and capture of that heart chamber traverses the non-paced pace/sense electrode after a delay that enables it to be sensed and mistakenly characterized as a refractory sense event Similarly, the delayed right-to-left or left-to-right conduction of a spontaneous depolarization occurring first in the right or left heart chamber, respectively, traverses the second pace/sense electrode after a delay that enables it to be sensed again and mistakenly characterized the second time as a refractory sense. Here also, a second restarting of post-event time periods due to a mistakenly characterized refractory sense event can result in the failure to respond appropriately to the next true, spontaneous sense event in either of the right and left heart chambers. Thus, the timing of delivery of bi-atrial or bi-ventricular pacing pulses can also be disrupted.

Similar problems arise in AV sequential, bi-atrial and/or bi-ventricular pacing systems of the types described above. A V-A pacing escape interval is typically restarted by one of the following events: delivery of a ventricular pacing pulse at the time-out of an AV delay; a spontaneous, non-refractory, ventricular sense event sensed in one ventricle before the time-out of the AV delay; or a spontaneous, non-refractory, ventricular sense event sensed in one ventricle before the time-out of the V-A escape interval. A set of post-ventricular event timers are started upon each such event and time out post-ventricular event periods, e.g. atrial and ventricular blanking periods and refractory periods and the URI. The post-ventricular event timers start at least one post-ventricular event period that affects the treatment of an atrial sense event occurring during its time-out. For example, an atrial sense event occurring during the time-out of a post-ventricular atrial refractory period (PVARP) can be ignored for purposes of resetting the V-A escape interval and starting the AV delay. The PVARP is typically programmable and can be set to prevent any response to an atrial sense event that may be caused by sensing of the antegrade conduction of the spontaneous or evoked ventricular depolarization through the atria and to the atrial pace/sense electrodes.

The PVARP, VRP (Ventricular Refractory Period) and URI interval are restarted each time that a ventricular pacing pulse is delivered and whenever a refractory or non-refractory ventricular sense event occurs. It is important to note that the hearts of patients in CHF frequently exhibit wide QRS complexes and prolonged conduction delays of up to 200 msec between electrodes implanted in relation to the right and left ventricles. This prolonged delay results in the possibility of sensing right and left ventricular sense events caused by the same spontaneous ventricular depolarization at times that are so separated that the second ventricular sense event restarts the post-event time periods, particularly the PVARP, that were started upon the earlier ventricular sense event of the same depolarization. The restarting of the PVARP can cause a true atrial sense event to be mistakenly characterized as a refractory atrial sense event which cannot terminate the V-A escape interval and restart the AV delay. This can cause loss of atrial and ventricular synchronization and effectively reduces the atrial rate that can be tracked. The restarting of the URI can lead to the extension of the AV delay, and the restarting of the VRP can cause a true ventricular depolarization to be characterized as a refractory ventricular sense event.

Similar timing problems may occur if triggered pacing pulses are delivered at multiple sites in a single heart chamber, and other timing issues occur with restarting of pacing escape intervals in any of the above described situations. These problems and how we address them are described within.

SUMMARY OF THE INVENTION

The present invention is therefore directed to providing multi-site pacing in a single heart chamber or right and left heart chamber pacing methods and systems that avoid prolonging post-event timing periods that cause pacing to be inhibited or to revert to asynchronous pacing because of a delayed conduction of a single depolarization between sense sites in the same or the right and left heart chambers.

In accordance with the invention, the delivery of a pacing pulse at the time-out of a preceding pacing escape interval or a non-refractory right or left chamber sense event during the pacing escape interval restarts the pacing escape interval, typical post-pace or post-sense time periods, and a conditional refractory period. The conditional refractory period is set to embrace the delayed conduction time of an abnormally conducted depolarization between spaced apart sense sites in the same or the right and left heart chambers.

A sense event that occurs during the conditional refractory period is treated as a refractory sense event and extends, e.g., by restarting, the post-sense periods except for the conditional refractory period. But, the restarted post-sense time periods are adjusted in relation to the time of occurrence of the refractory sense event within the conditional refractory period. The restarted post-sense time periods are preferably shortened by the elapsed time of the conditional refractory period. The shortened post-sense periods enable appropriate response to noise if further sense events occur during time-out of the restarted post-sense periods but are not so prolonged as to prevent legitimate sense events from restarting the pacing escape interval.

The present invention is preferably implemented in pacing systems for pacing and sensing at spaced apart pace/sense electrode sites in a single heart chamber or pacing and sensing at pace/sense electrode sites in right and left heart chambers to provide bi-atrial and/or bi-ventricular pacing.

The present invention has a number of advantages flowing from negating the extension of the post-event time periods in response to a sense event occurring within the conditional refractory period. A principal advantage is that a subsequent true sense event occurring after the time-out of the post-event time periods will not be characterized as a refractory sense event as it would have been if the post-event time periods were restarted for their full length. However, the post-event time periods are restarted for their full lengths if a second sense event occurs during their time-out, on the assumption that the closely timed first and second refractory sense events represent noise.

Other advantages include the ability to accumulate data related to the occurrences of refractory sense events during the conditional refractory period and closely following its time-out for diagnostic purposes. The occurrences of refractory sense events and their timing within the conditional refractory period and outside the conditional refractory period can be retained in in Implantable Pulse Generator (IPG) memory for retrieval and analysis at a later time or may be used by on-board algorithms to adjust pacing and sensing parameters. For example, the data may be useful in determining that loss of capture has occurred when a pacing pulse is followed by a refractory sense event within the conditional refractory period. The pacing pulse energy can be increased either automatically or by a physician upon reviewing the retrieved data. Or, the conditional refractory period may be automatically extended or extended by the physician upon reviewing the data if refractory sense events following a non-refractory sense event tend to first occur just after the end of the conditional refractory period.

The present invention is preferably implemented into an external or implantable pulse generator and lead system selectively employing right and left heart, atrial and/or ventricular leads. The preferred embodiment is implemented in an architecture that allows wide programming flexibility for operating in AV synchronous modes with right and left ventricular pacing or in atrial or ventricular only modes for providing only right and left atrial or ventricular pacing. The AV synchronous embodiments may be implemented into an IPG or external pulse generator and lead system providing right and left ventricular pacing and sensing and either both right and left atrial pacing or just right or left atrial pacing and sensing. Alternatively, the invention can be implemented in IPGs or external pulse generators and lead systems having hard wired connections and operating modes that are not as programmable.

BRIEF DESCRIPTION OF THE DRAWINGS

These and other advantages and features of the present invention will be more readily understood from the following detailed description of the preferred embodiments thereof, when considered in conjunction with the drawings, in which like reference numerals indicate identical structures throughout the several views, and wherein.

DETAILED DESCRIPTION OF THE PREFERRED EMBODIMENTS

In the following detailed description, references are made to illustrative embodiments for carrying out the invention. It is understood that other embodiments may be utilized without departing from the scope of the invention. For example, the invention is disclosed in detail in FIGS. 2 and 3 in the context of an AV sequential, bi-ventricular, pacing system operating in demand, atrial tracking, and triggered pacing modes in accordance with FIG. 4 for restoring synchrony in depolarizations and contraction of left and right ventricles in synchronization with atrial sensed and paced events for treating bradycardia in those chambers. This embodiment of the invention is programmable to operate as a three channel pacing system having an AV synchronous operating mode for restoring upper and lower heart chamber synchronization and right and left ventricular chamber depolarization synchrony. But, it will be realized that the invention can also be practiced in a bi-ventricular or bi-atrial pacing system that can be dedicated to such use or can be a programmable mode of the system of FIGS. 2 and 3 following the flow chart of FIG. 9. In either case, the steps of delivering right and/or left chamber pacing illustrated in FIGS. 5 and 6A–6B and the conditional refractory period processing steps of FIG. 7 can be employed. The invention can be practiced in a two channel or four channel pacing system of the type disclosed in the above-incorporated '324 patent as well.

Figure 9:
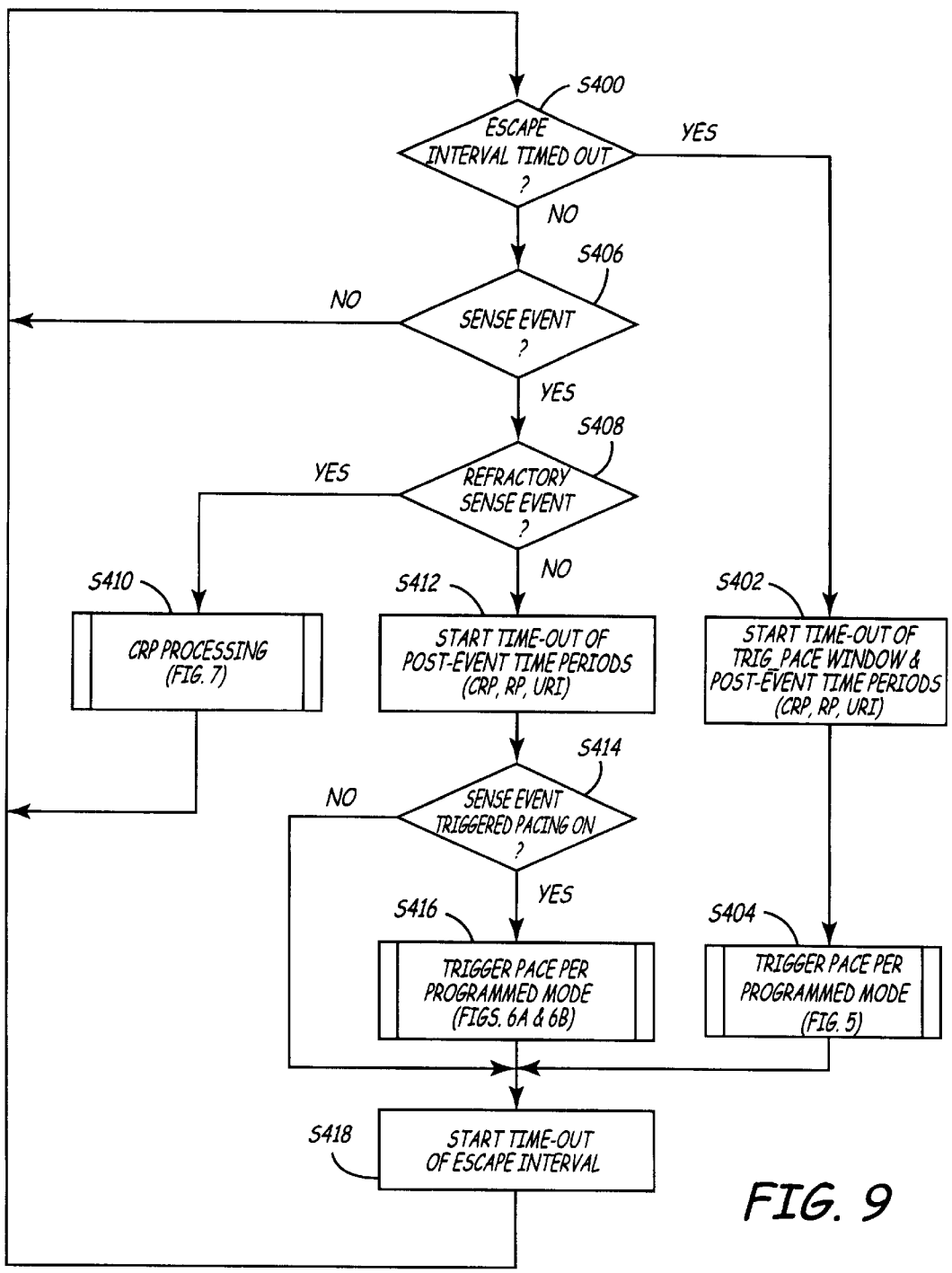
FIG. 9 is a comprehensive flow-chart illustrating the operating modes of the IPG circuitry of FIG. 3 in a variety of single chamber or bi-atrial or bi-ventricular pacing modes in accordance with a further embodiment of the invention selectively employing steps of FIGS. 5–7 therein.

Moreover, the invention can be practiced in a pacemaker providing pacing and sensing at multiple spaced apart pace/ sense electrode sites in a single heart chamber following the steps of FIG. 9. It should also be appreciated that the present invention may be incorporated into an anti-tachyarrhythmia system including specific high rate pacing and cardioversion shock therapies for providing staged therapies to treat a diagnosed arrhythmia.

In patients suffering from CHF, the hearts may become dilated, and the conduction and depolarization sequences of the heart chambers may exhibit Intra-Atrial Conduction Defects (IACD), Left Bundle Branch Block (LBBB), Right Bundle Branch Block (RBBB), and Intra Ventricular Conduction Defects (IVCD). Single and AV synchronous pacing of the right atrium and/or right ventricle can be counterproductive in such cases, depending on the defective conduction pathway and the locations of the pace/sense electrodes. It should be appreciated that the present invention may be utilized particularly to treat patients suffering from CHF with or without bradycardia. The pacing system of the present invention may also may be incorporated into an anti-tachyarrhythmia system including specific high rate pacing and cardioversion shock therapies for providing staged therapies to treat a diagnosed arrhythmia.

Figure 1:
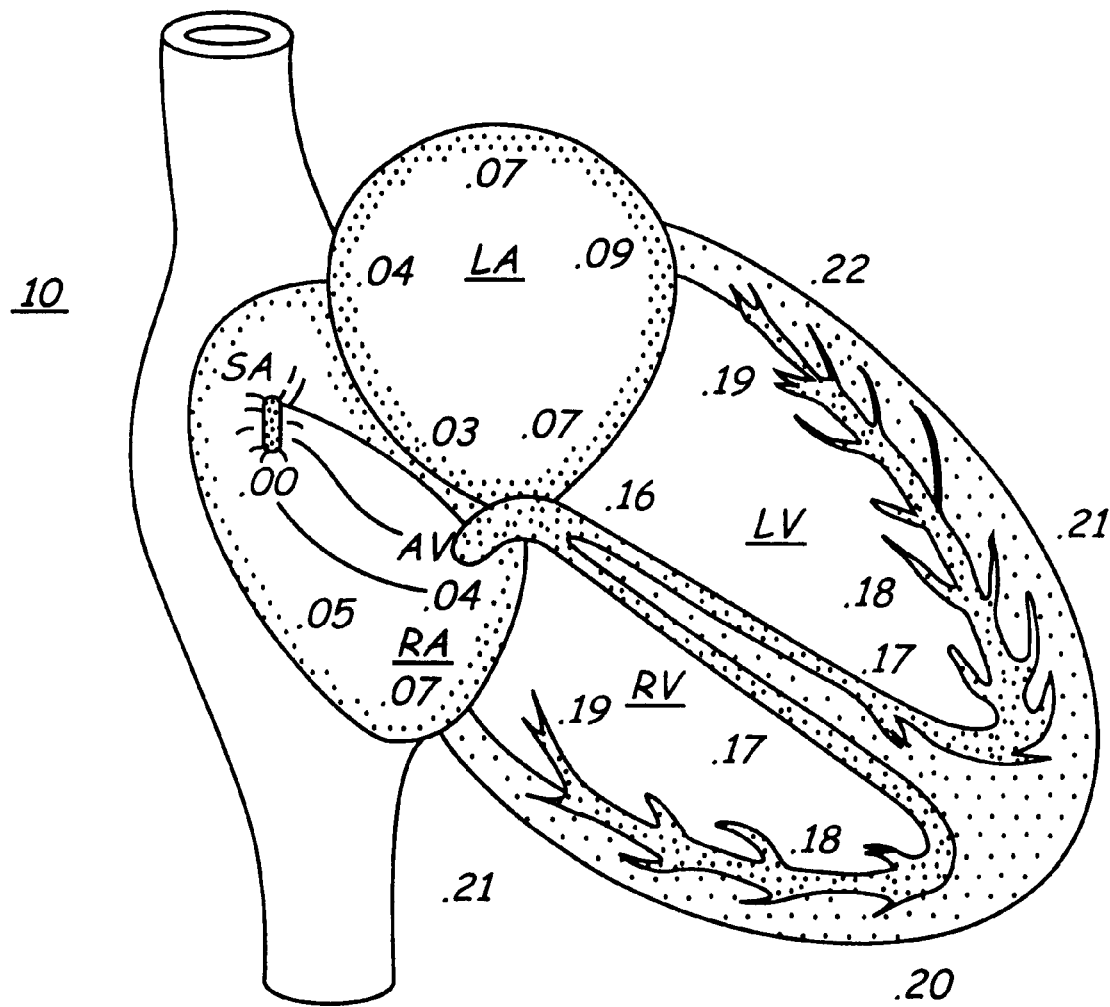
FIG. 1 is an illustration of transmission of the cardiac depolarization waves through the heart in a normal electrical activation sequence.

In FIG. 1, heart 10 includes the upper heart chambers, the right atrium (RA) and left atrium (LA), and the lower heart chambers, the right ventricle (RV) and left ventricle (LV) and the coronary sinus (CS) extending from the opening in the right atrium laterally around the atria to form the cardiac veins. FIG. 1 is an illustration of transmission of the cardiac depolarization waves through the RA, LA, RV and LV in a normal electrical activation sequence at a normal heart rate with the conduction times exhibited thereon in seconds. The cardiac cycle commences normally with the generation of the depolarization impulse at the SA Node in the right atrial wall and its transmission through the atrial conduction pathways of Bachmann's Bundle and the Internodal Tracts at the atrial level into the left atrial septum. The RA depolarization wave reaches the Atrio-ventricular (AV) node and the atrial septum within about 40 msec and reaches the furthest walls of the RA and LA within about 70 msec, and the atria complete their contraction as a result. The aggregate RA and LA depolarization wave appears as the P-wave of the PQRST complex when sensed across external ECG electrodes and displayed. The component of the atrial depolarization wave passing between a pair of unipolar or bipolar pace/sense electrodes, respectively, located on or adjacent the RA or LA is also referred to as a sensed P-wave. Although the location and spacing of the external ECG electrodes or implanted unipolar atrial pace/sense electrodes has some influence, the normal P-wave width does not exceed 80 msec in width as measured by a high impedance sense amplifier coupled with such electrodes. A normal near field P-wave sensed between closely spaced bipolar pace/sense electrodes and located in or adjacent the RA or the LA has a width of no more than 60 msec as measured by a high impedance sense amplifier.

The depolarization impulse that reaches the AV Node is distributed inferiorly down the bundle of His in the intra-ventricular septum after a delay of about 120 msec. The depolarization wave reaches the apical region of the heart about 20 msec later and then travels superiorly though the Purkinje Fiber network over the remaining 40 msec. The aggregate RV and LV depolarization wave and the subsequent T-wave accompanying re-polarization of the depolarized myocardium are referred to as the QRST portion of the PQRST cardiac cycle complex when sensed across external ECG electrodes and displayed. When the amplitude of the QRS ventricular depolarization wave passing between a bipolar or unipolar pace/sense electrode pair located on or adjacent the RV or LV exceeds a threshold amplitude, it is detected as a sensed R-wave. Although the location and spacing of the external ECG electrodes or implanted unipolar ventricular pace/sense electrodes has some influence, the normal R-wave width does not exceed 80 msec in width as measured by a high impedance sense amplifier. A normal near field R-wave sensed between closely spaced bipolar pace/sense electrodes and located in or adjacent the RV or the LV has a width of no more than 60 msec as measured by a high impedance sense amplifier.

The typical normal conduction ranges of sequential activation are also described in the article by Durrer et al., entitled "Total Excitation of the Isolated Human Heart", in CIRCULATION (Vol. XLI, pp. 899–912, June 1970). This normal electrical activation sequence becomes highly disrupted in patients suffering from advanced CHF and exhibiting IACD, LBBB, RBBB, and/or IVCD. These conduction defects exhibit great asynchrony between the RV and the LV due to conduction disorders along the Bundle of His, the Right and Left Bundle Branches or at the more distal Purkinje Terminals. Typical intra-ventricular peak-peak asynchrony can range from 80 to 200 msec or longer. In RBBB and LBBB patients, the QRS complex is widened far beyond the normal range to from >120 msec to 250 msec as measured on surface ECG. This increased width demonstrates the lack of synchrony of the right and left ventricular depolarizations and contractions.

In accordance with the present invention, a method and apparatus is provided to restore the depolarization sequence of FIG. 1 and the synchrony between the right and left ventricular heart chambers that contributes to adequate cardiac output. This restoration is effected through providing optimally timed cardiac pacing pulses to the right and left ventricles as necessary and to account for the particular implantation sites of the pace/sense electrodes in relation to each heart chamber while maintaining AV synchrony. The present invention avoids complications arising from double sensing of wide QRS complexes that can disrupt AV synchrony by use of a CVRP as described further below.

Figure 2:
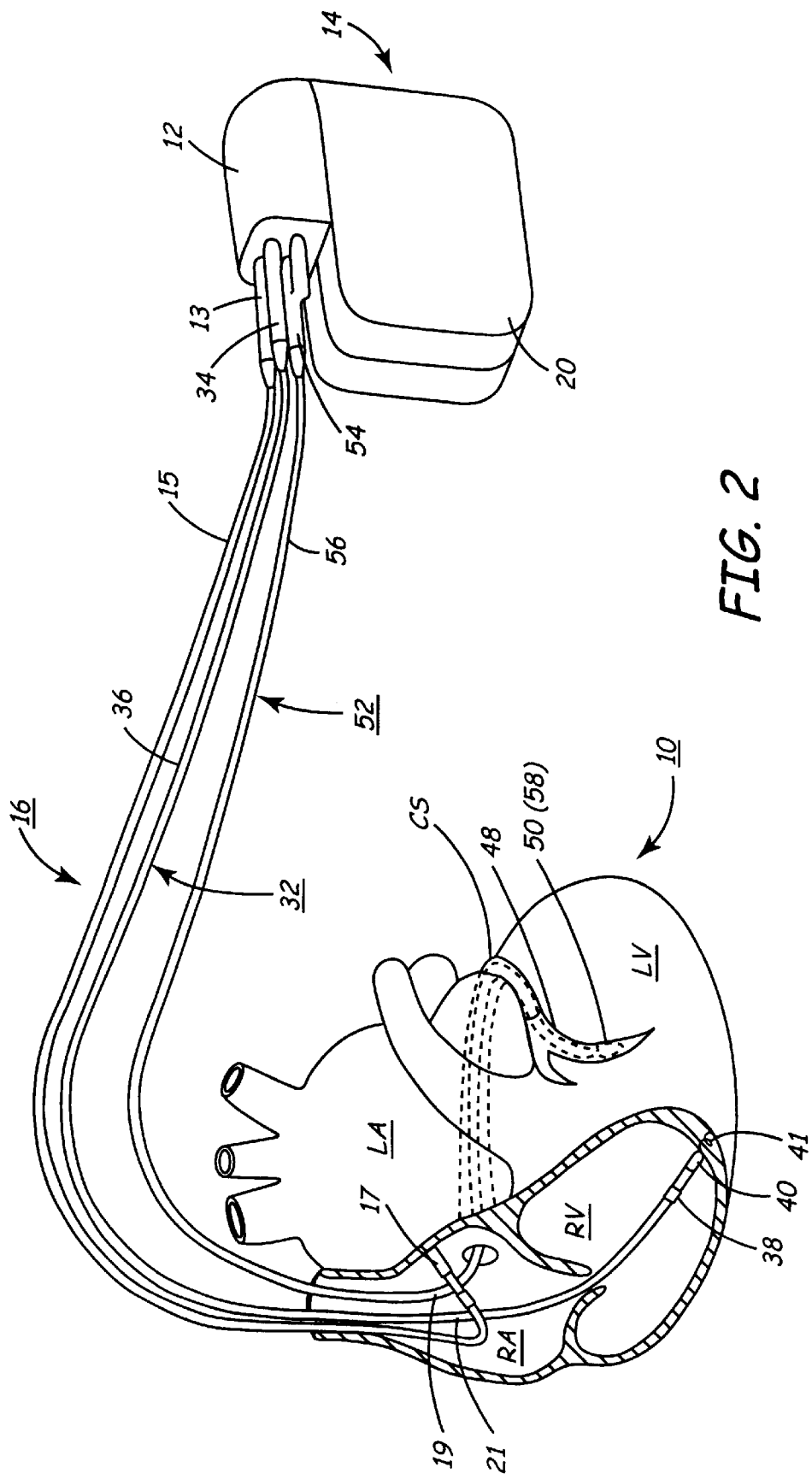
FIG. 2 is a schematic diagram depicting a three channel, atrial and bi-ventricular, pacing system in which the present invention is preferably implemented.

FIG. 2 is a schematic representation of an implanted, three channel cardiac pacemaker of the above noted types for restoring AV synchronous contractions of the atrial and ventricular chambers and simultaneous or sequential pacing of the right and left ventricles. The implantable pulse generator IPG 14 is implanted subcutaneously in a patient's body between the skin and the ribs. Three endocardial leads 16, 32 and 52 connect the IPG 14 with the RA, the RV and the LV, respectively. Each lead has at least one electrical conductor and pace/sense electrode, and a remote indifferent electrode 20 is formed as part of the outer surface of the housing of the IPG 14. As described further below, the pace/sense electrodes and the remote indifferent electrode 20 (IND_CAN electrode) can be selectively employed to provide a number of unipolar and bipolar pace/sense electrode combinations for pacing and sensing functions. The depicted positions in or about the right. and left heart chambers are also merely exemplary. Moreover other leads and pace/sense electrodes may be used instead of the depicted leads and pace/sense electrodes that are adapted to be placed at electrode sites on or in or relative to the RA, LA, RV and LV.

The depicted bipolar endocardial RA lead 16 is passed through a vein into the RA chamber of the heart 10, and the distal end of the RA lead 16 is attached to the RA wall by an attachment mechanism 17. The bipolar endocardial RA lead 16 is formed with an in-line connector 13 fitting into a bipolar bore of IPG connector block 12 that is coupled to a pair of electrically insulated conductors within lead body 15 and connected with distal tip RA pace/sense electrode 19 and proximal ring RA pace/sense electrode 21. Delivery of atrial pace pulses and sensing of atrial sense events is effected between the distal tip RA pace/sense electrode 19 and proximal ring RA pace/sense electrode 21, wherein the proximal ring RA pace/sense electrode 21 functions as an indifferent electrode (IND_). Alternatively, a unipolar endocardial RA lead could be substituted for the depicted bipolar endocardial RA lead 16 and be employed with the IND_CAN electrode 20. Or, one of the distal tip RA pace/sense electrode 19 and proximal ring RA pace/sense electrode 21 can be employed with the IND_CAN electrode 20 for unipolar pacing and/or sensing.

Bipolar, endocardial RV lead 32 is passed through the vein and the RA chamber of the heart 10 and into the RV where its distal ring and tip RV pace/sense electrodes 38 and 40 are fixed in place in the apex by a conventional distal attachment mechanism 41. The RV lead 32 is formed with an in-line connector 34 fitting into a bipolar bore of IPG connector block 12 that is coupled to a pair of electrically insulated conductors within lead body 36 and connected with distal tip RV pace/sense electrode 40 and proximal ring RV pace/sense electrode 38, wherein the proximal ring RV pace/sense electrode 38 functions as an indifferent electrode (IND_RV). Alternatively, a unipolar endocardial RV lead could be substituted for the depicted bipolar endocardial RV lead 32 and be employed with the IND_CAN electrode 20. Or, one of the distal tip RV pace/sense electrode 40 and proximal ring RV pace/sense electrode 38 can be employed with the IND_CAN electrode 20 for unipolar pacing and/or sensing.

In this illustrated embodiment, a unipolar, endocardial LV CS lead 52 is passed through a vein and the RA chamber of the heart 10, into the CS and then inferiorly in a coronary venous branch 48 to extend the distal LV CS pace/sense electrode 50 alongside the LV chamber. The LV CS lead 52 is formed with a small diameter single conductor lead body 56 coupled at the proximal end connector 54 fitting into a bore of IPG connector block 12. A small diameter unipolar lead body 56 is selected in order to lodge the distal LV CS pace/sense electrode 50 in a vein branching inferiorly from the coronary sinus 48. Numerous other embodiments using epicardial leads or even patch electrodes used for cardio defibrillators could be employed with similar effect, and they could be bi-polar or even multi-polar if desired. The use of unipolar epicardial lead as shown is simply the most likely implementation, but that will vary with the condition of the patient and the heart, as well as with what is available and what other conditions and devices are considered.

The distal LV CS pace/sense electrode 50 can be paired with the proximal ring RV pace/sense electrode 38 or the IND_CAN electrode 20 for unipolar pacing and/or sensing. Alternatively, the distal LV CS pace/sense electrode 50 can be paired with the distal tip RV pace/sense electrode 40 for sensing across the RV and LV as described further below. In addition, LV CS lead 52 can comprise a bipolar endocardial lead having an LV ring electrode 58 located proximally to distal tip electrode 50 as shown in FIG. 3 and described further below, so as to allow for maximal flexibility in selection of pacing and sensing electrode pairs for LV pacing and sensing.

Moreover, in a four chamber embodiment, LV CS lead 52 could bear a proximal one or a pair of LA CS pace/sense electrodes positioned along the lead body to lie in the larger diameter coronary sinus CS adjacent the LA. In that case, the lead body 56 would encase two or three electrically insulated lead conductors extending from the more proximal LA CS pace/sense electrode(s) and terminating in a bipolar or tripolar connector 54.

These described RA and LA and RV and LV pace/sense leads and electrode locations are merely exemplary of possible leads and electrode locations that can be employed in the practice of these embodiments of the present invention. It will be understood that one or more of the other types of endocardial and epicardial leads and pace/sense electrodes located in or about the right and left chambers of the heart can be substituted for those illustrated in FIG. 2 and described above.

Figure 3:
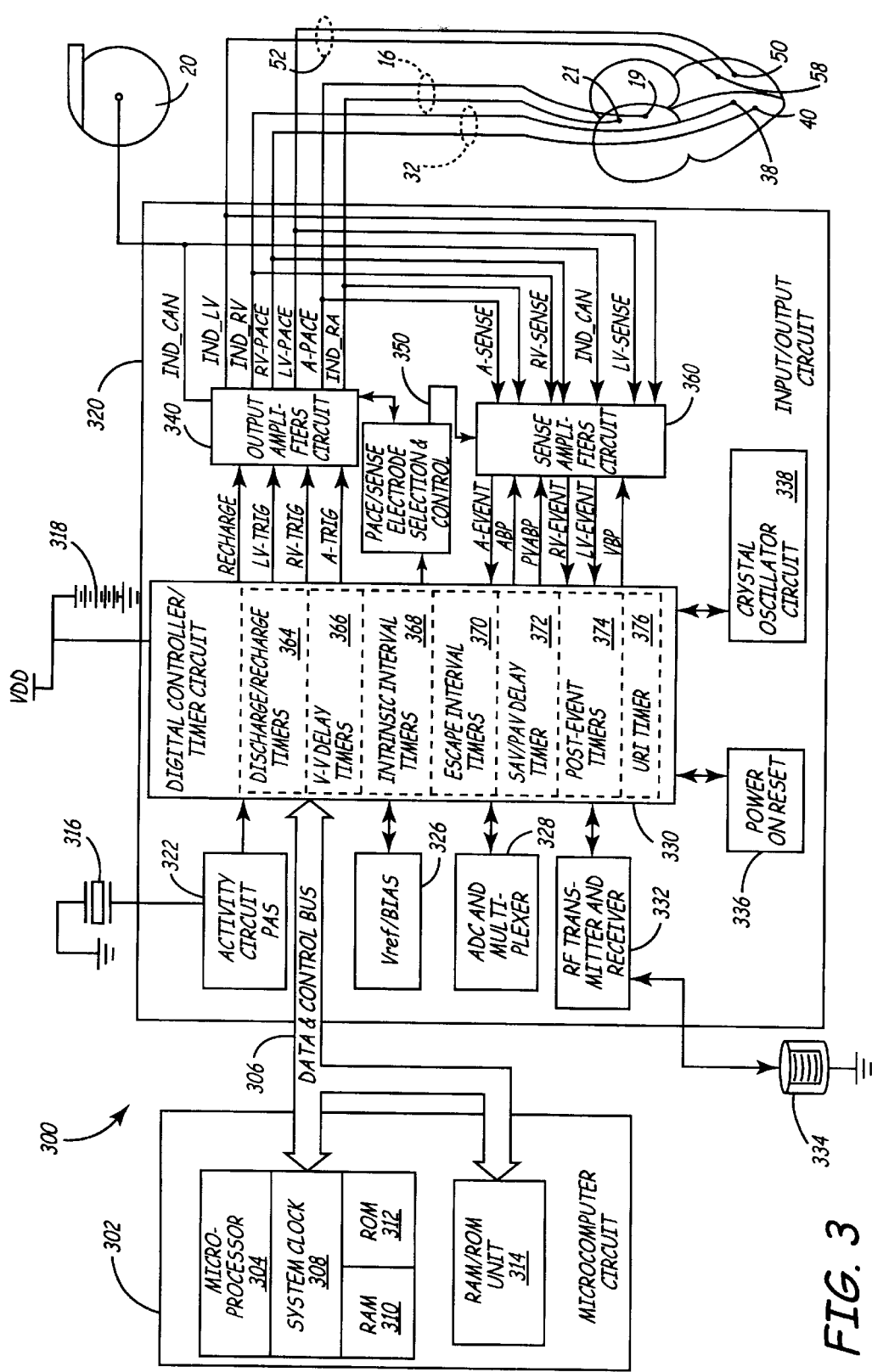
FIG. 3 is a simplified, functional block diagram of one embodiment of IPG circuitry and associated leads employed in the system of FIG. 2 for providing three pacing channels that are selectively programmed for selectively pacing and sensing depolarizations of the right and left ventricles in synchrony with pacing and sensing depolarizations of the atria.

Typically, in pacing systems of the type illustrated in FIGS. 2 and 3, the electrodes designated above as "pace/sense" electrodes are used for both pacing and sensing functions. In accordance with one aspect of the present invention, these "pace/sense" electrodes can be selected to be used exclusively as pace or sense electrodes or to be used in common as pace/sense electrodes in programmed combinations for sensing cardiac signals and delivering pacing pulses along pacing and sensing vectors. Separate or shared indifferent pace and sense electrodes can also be designated in pacing and sensing functions. For convenience, the following description separately designates pace and sense electrode pairs where a distinction is appropriate.

FIG. 3 depicts atrial and ventricular leads 16, 32, and 52 coupled with an IPG circuit 300 having programmable modes and parameters and a telemetry transceiver of a DDDR type known in the pacing art. The IPG circuit 300 is illustrated in a functional block diagram divided generally into a microcomputer circuit 302 and a pacing circuit 320. The pacing circuit 320 includes the digital controller/timer circuit 330, the output amplifiers circuit 340, and the sense amplifiers circuit 360, as well as a number of other circuits and components described below.

Crystal oscillator circuit 338 provides the basic timing clock for the pacing circuit 320, while battery 318 provides power. Power-on-reset circuit 336 responds to initial connection of the circuit to the battery for defining an initial operating condition and similarly, resets the operative state of the device in response to detection of a low battery condition. Reference mode circuit 326 generates stable voltage reference and currents for the analog circuits within the pacing circuit 320, while analog to digital converter ADC and multiplexer circuit 328 digitizes analog signals and voltage to provide real time telemetry if a cardiac signals from sense amplifiers 360, for uplink transmission via RF transmitter and receiver circuit 332. Voltage reference and bias circuit 326, ADC and multiplexer 328, power-on-reset circuit 336 and crystal oscillator circuit 338 may correspond to any of those presently used in current marketed implantable cardiac pacemakers.

If the IPG is programmed to a rate responsive mode, the signals output by one or more physiologic sensor are employed as a rate control parameter (RCP) to derive a physiologic escape interval. For example, the escape interval is adjusted proportionally the patient's activity level developed in the patient activity sensor (PAS) circuit 322 in the depicted, exemplary IPG circuit 300. The patient activity sensor 316 is coupled to the implantable pulse generator housing 118 and may take the form of a piezoelectric crystal transducer as is well known in the art and its output signal is processed and used as the RCP. A timed interrupt, e.g., every two seconds, may be provided in order to allow the microprocessor 304 to analyze the output of the activity circuit PAS 322 and update the basic V-A (or A-A or V-V) escape interval employed in the pacing cycle.

Data transmission to and from the external programmer is accomplished by means of the telemetry antenna 334 and an associated RF transmitter and receiver 332, which serves both to demodulate received downlink telemetry and to transmit uplink telemetry. Uplink telemetry capabilities will typically include the ability to transmit stored digital information, e.g. operating modes and parameters, EGM histograms, and other events, as well as real time EGMs of atrial and/or ventricular electrical activity and Marker Channel pulses indicating the occurrence of sensed and paced depolarizations in the atrium and ventricle, as are well known in the pacing art.

Microcomputer 302 contains a microprocessor 304 and associated system clock 308 and on-processor RAM and ROM chips 310 and 312, respectively. In addition, microcomputer circuit 302 includes a separate RAM/ROM chip 314 to provide additional memory capacity. Microprocessor 304 normally operates in a reduced power consumption mode and is interrupt driven. Microprocessor 304 is awakened in response to defined interrupt events, which may include A-PACE, RV-PACE, LV-PACE signals generated by timers in digital timer/controller circuit 330 and A-EVENT, RV-EVENT, and LV-EVENT signals generated by sense amplifiers circuit 360, among others. The specific values of the intervals and delays timed out by digital controller/timer circuit 330 are controlled by the microcomputer circuit 302 by means of data and control bus 306 from programmed-in parameter values and operating modes.

In one embodiment of the invention, microprocessor 304 is a custom microprocessor adapted to fetch and execute instructions stored in RAM/ROM unit 314 in a conventional manner. It is contemplated, however, that other implementations may be suitable to practice the present invention. For example, an off-the-shelf, commercially available microprocessor or microcontroller, or custom application-specific, hardwired logic, or state-machine type circuit may perform the functions of microprocessor 304.

Digital controller/timer circuit 330 operates under the general control of the microcomputer 302 to control timing and other functions within the pacing circuit 320 and includes a set of timing and associated logic circuits of which certain ones pertinent to the present invention are depicted. The depicted timing circuits include discharge/recharge timers 364, V-V delay timer 366, an intrinsic interval timer 368 for timing elapsed V-EVENT to V-EVENT intervals or V-EVENT to A-EVENT intervals, escape interval timers 370 for timing A-A, V-A, and/or V-V pacing escape intervals, an AV delay interval timer 372 for timing an AV delays from a preceding A-EVENT (SAV) or A-PACE (PAV), a post-ventricular event timer 374 for timing post-ventricular time periods, and URI timer 376 for timing the URI.

Microcomputer 302 controls the operational functions of digital controller/timer circuit 330, specifying which timing intervals are employed, and setting at least the programmed-in base timing intervals, via data and control bus 306. Digital controller/timer circuit 330 starts and times out these intervals and delays for controlling operation of the atrial and ventricular sense amplifiers in sense amplifiers circuit 360 and the atrial and ventricular pace pulse generators in output amplifiers circuit 340.

The post-event timers 374 time out the post-ventricular time periods following an RV-EVENT or LV-EVENT or a RV-PACE or LV-PACE and post-atrial time periods following an A-EVENT or A-PACE. The durations of the post-event time periods may also be selected as programmable parameters stored in the microcomputer 302. The post-ventricular time periods include the PVARP, a post-atrial ventricular blanking period (PAVBP), a ventricular blanking period (VBP), a ventricular refractory period (VRP), and a CVRP. The post-atrial time periods include an atrial refractory period (ARP) during which an A-EVENT is ignored for the purpose of resetting the AV delay, and an atrial blanking period (ABP) during which atrial sensing is disabled. These post-atrial time periods time out concurrently with the time-out of the SAV or PAV delay started by an A-EVENT or an A-PACE.

It should be noted that the starting of the post-atrial time periods and the AV delays can be commenced substantially simultaneously with the start or end of the A-EVENT or A-PACE. Similarly, the starting of the post-ventricular time periods and the V-A escape interval can be commenced substantially simultaneously with the start or end of the V-EVENT or V-PACE.

The microprocessor 304 also optionally calculates AV delays, post-ventricular time periods, and post-atrial time periods which vary with the sensor based escape interval established in response to the RCP(s) and/or with the intrinsic atrial rate. The variable AV delays are usually derived as a fraction of a maximum AV delay set for the pacing lower rate (i.e., the longest escape interval).

The output amplifiers circuit 340 contains a RA pace pulse generator, a RV pace pulse generator and a LV pace pulse generator or corresponding to any of those presently employed in commercially marketed cardiac pacemakers providing atrial and ventricular pacing. In order to trigger generation of an RV-PACE or LV-PACE pulse, digital controller/timer circuit 330 generates a RV-TRIG or LV-TRIG signal at the end of an AV delay provided by AV delay interval timer 372. Similarly, in order to trigger an atrial pacing or A-PACE pulse, digital controller/timer circuit 330 generates an A-TRIG signal at the end of the V-A escape interval timed by escape interval timers 370. The output amplifiers circuit 340 also includes switching circuits for coupling selected pacing output pairs from among the lead conductors and the IND_CAN electrode 20 to the RA pace pulse generator, RV pace pulse generator and LV pace pulse generator. Pace/sense electrode pair selection and control circuit 350 selects lead conductors and associated pacing electrode pairs to be coupled with the atrial and ventricular output amplifiers within output amplifiers circuit 340 for accomplishing RA, RV and LV pacing as described below.

The sense amplifiers circuit 360 contains sense amplifiers corresponding to any of those presently employed in commercially marketed cardiac pacemakers for atrial and ventricular pacing and sensing. As noted in the above-referenced, commonly assigned, '324 patent, it has been common in the prior art to use very high impedance P-wave and R-wave sense amplifiers to amplify the voltage difference signal which is generated across the sense electrode pairs by the passage of a cardiac depolarization. The high impedance sense amplifiers use high gain to amplify the low amplitude signals and rely on pass band filters, time domain filtering and amplitude threshold comparison to discriminate a P-wave or R-wave from background electrical noise. Digital controller/timer circuit 330 controls sensitivity settings of the atrial and ventricular sense amplifiers 360.

The sense amplifiers are uncoupled from the sense electrodes during the blanking periods before, during, and after delivery of a pacing pulse to any of the pace electrodes of the pacing system to avoid saturation of the sense amplifiers.

The sense amplifiers circuit 360 includes blanking circuits for uncoupling the selected pairs of the lead conductors and the IND_CAN electrode 20 from the inputs of the RA sense amplifier, RV sense amplifier and LV sense amplifier during the ABP, PVABP and VBP. The sense amplifiers circuit 360 also includes switching circuits for coupling selected sense electrode lead conductors and the IND_CAN electrode 20 to the RA sense amplifier, RV sense amplifier and LV sense amplifier. Again, sense electrode selection and control circuit 350 selects conductors and associated sense electrode pairs to be coupled with the atrial and ventricular sense amplifiers within the output amplifiers circuit 340 and sense amplifiers circuit 360 for accomplishing RA, RV and LV sensing along desired unipolar and bipolar sensing vectors.

Atrial depolarizations or P-waves in the A-SENSE signal that are sensed by an atrial sense amplifier result in an A-EVENT signal that is communicated to the digital controller/timer circuit 330. Ventricular depolarizations or R-waves in the RV-SENSE signal are sensed by a ventricular sense amplifier result in an RV-EVENT signal that is communicated to the digital controller/timer circuit 330. Similarly, ventricular depolarizations or R-waves in the LV-SENSE signal are sensed by a ventricular sense amplifier result in an LV-EVENT signal that is communicated to the digital controller/timer circuit 330. The RV-EVENT, LV-EVENT, and RA-EVENT signals may be refractory or non-refractory, and can inadvertently be triggered by electrical noise signals or aberrantly conducted depolarization waves rather than true R-waves or P-waves.

Figure 4:
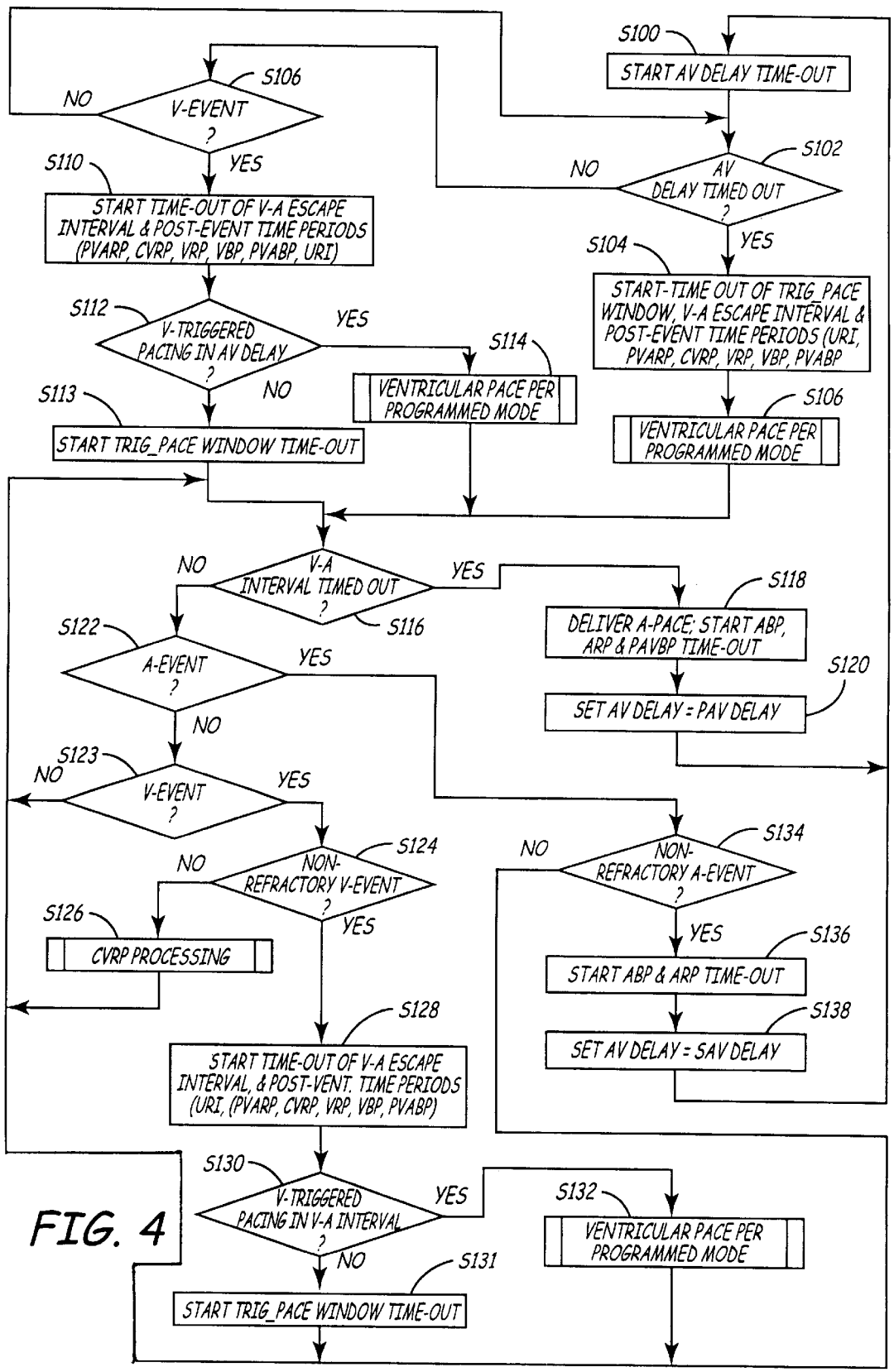
FIG. 4 is a comprehensive flow-chart illustrating the operating modes of the IPG circuitry of FIG. 3 in a variety of AV synchronous, bi-ventricular pacing modes in accordance with one embodiment of the invention.

The general operation of IPG circuit 300 is depicted in the flow chart of FIG. 4. The AV delay is started in step S100 when a P-wave outside of refractory is sensed across the selected RA sense electrodes (or LA sense electrodes if present) during the V-A escape interval (an A-EVENT) as determined in step S134 or an A-PACE pulse is delivered to the selected atrial pace electrode pair in step S118. The AV delay can be a PAV or SAV delay, depending upon whether it is started on an A-PACE or an A-EVENT, respectively, and is timed out by the SAV/PAV delay timer 372. The SAV or PAV delay is terminated upon a non-refractory RV-EVENT or LV-EVENT output by a ventricular sense amplifier prior to its time-out.

The post-event timers 374 are started to time out the post-ventricular time periods and the TRIG_PACE window, and the V-A escape interval timer 370 is started to time out the V-A escape interval in step S104 if the SAV or PAV delay times out in step S102 without the detection of a non-refractory RV-EVENT or LV-EVENT. The TRIG_PACE window inhibits triggered pacing modes in response to a sense event occurring too early in the escape interval and is described in greater detail in the above-referenced Ser. No. 09/439,078 application.

Figure 5:
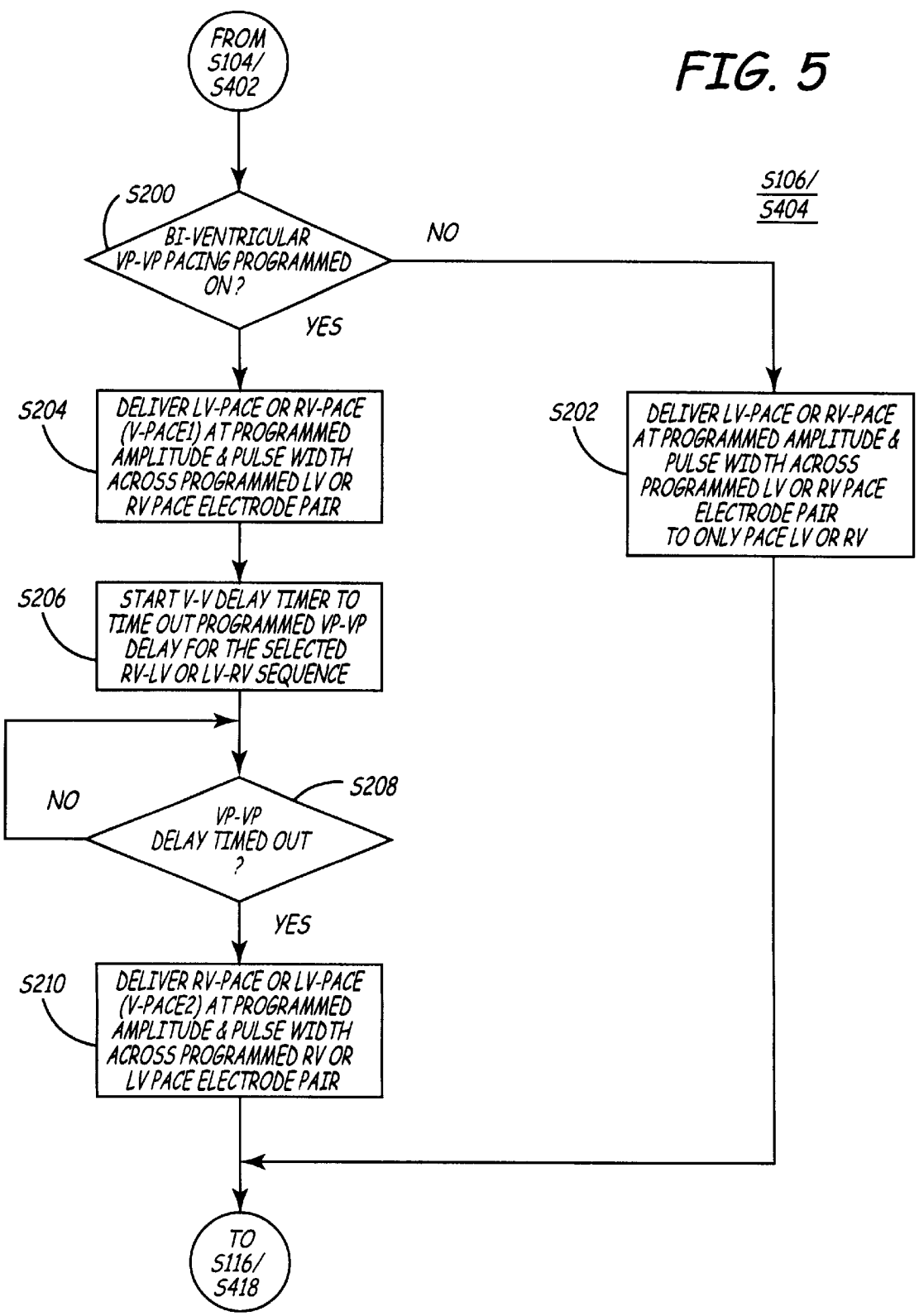
FIG. 5 is a flow chart illustrating the steps of delivering ventricular pacing pulses following time-out of an AV delay in FIG. 4.

Either a programmed one or both of the RV-PACE and LV-PACE pulses are delivered in step S106 (as shown in FIG. 5) to selected RV and LV pace electrode pairs, and the V-A escape interval timer is timed out in step S116. When both of the RV-PACE and LV-PACE pulses are delivered, the first is referred to as V-PACE1, the second is referred to as V-PACE2, and they are separated by a VP-VP delay. As described in greater detail below in reference to FIGS. 6A–6B, if a bi-ventricular pacing mode is programmed in step S106, it can be selectively programmed in a left-to-right or right-to-left ventricle pacing sequence wherein the first and second delivered ventricular pacing pulses are separated by separately programmed VP-VP delays. The VP-VP delays are preferably programmable between nearly 0 msec and about 80 msec.

Figure 6A:
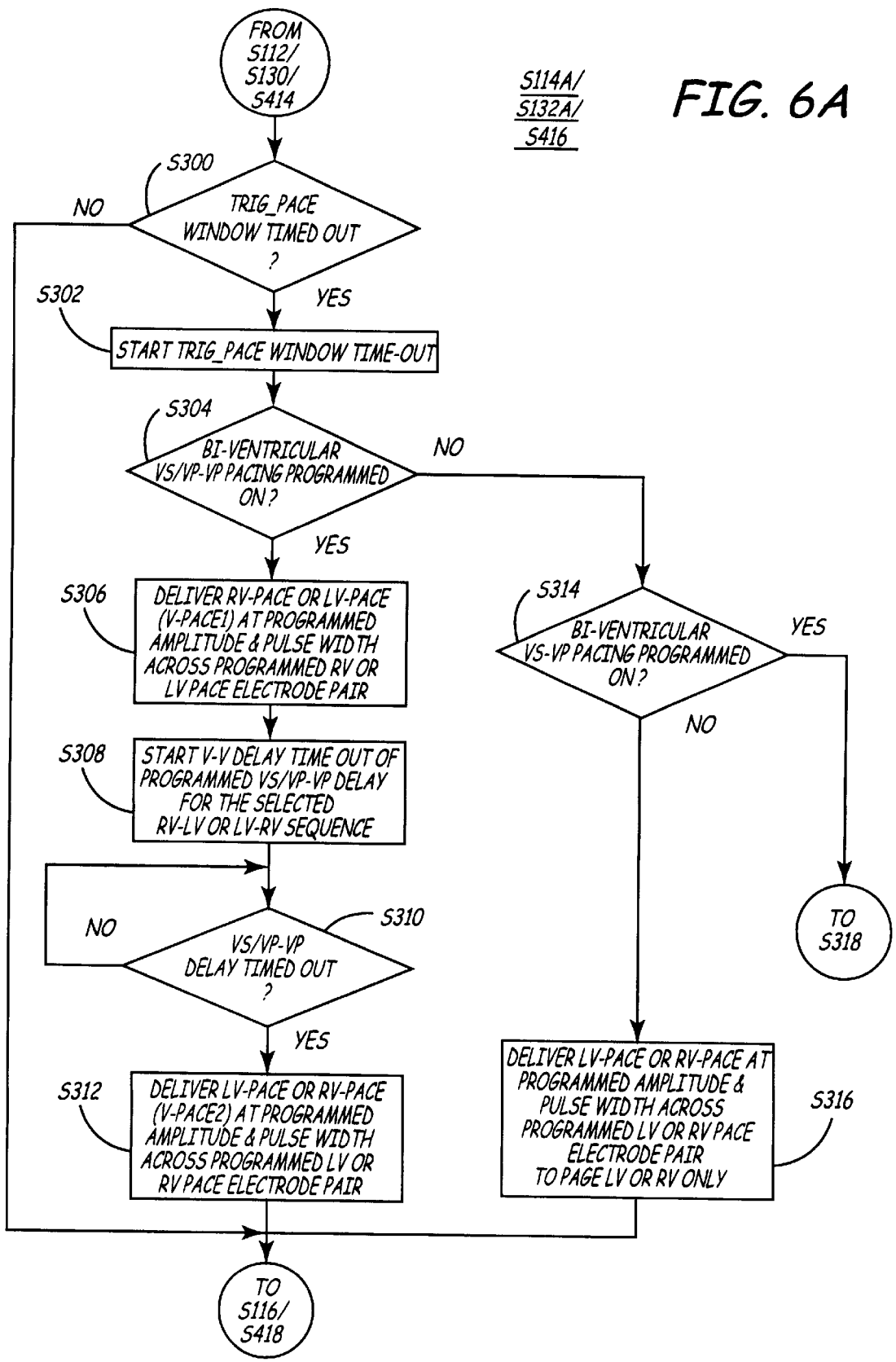
FIGS. 6A–6B is a flow chart illustrating the steps of delivering ventricular pacing pulses following a ventricular sense event during the time-out of an AV delay or the V-A escape interval in FIG. 4.
Figure 6B:
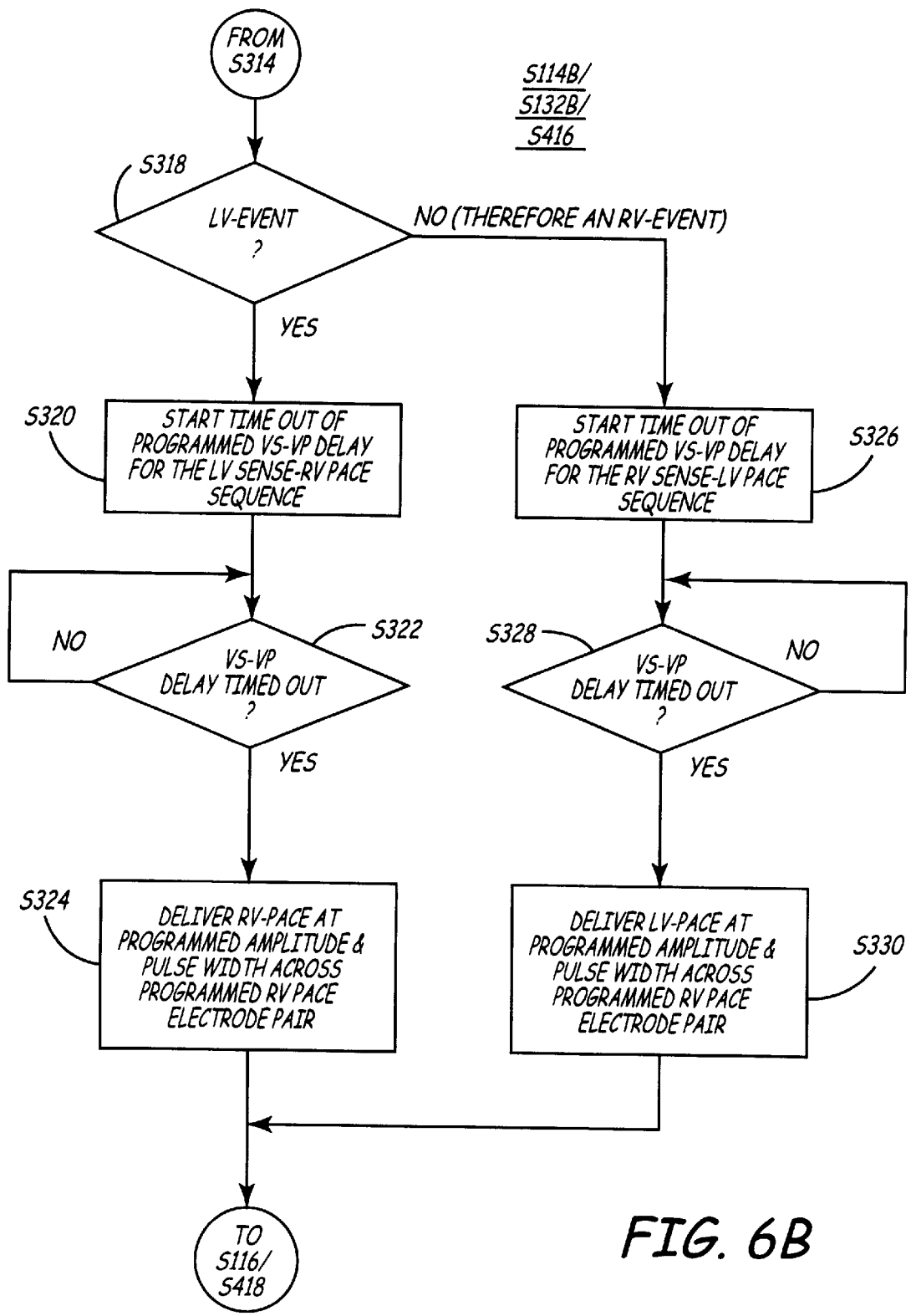

Returning to step S102, the AV delay is terminated if an RV-EVENT or LV-EVENT (collectively, a V-EVENT) is generated by the RV sense amplifier or the LV sense amplifier in step S108. The time-out of the V-A escape interval and the post-ventricular time periods are started in step S110 in response to the V-EVENT. In step S112, it is determined whether a ventricular triggered pacing mode is programmed to be operative during the AV delay. If one is programmed on, then it is undertaken and completed in step S114 (FIGS. 6A–6B). If a ventricular triggered pacing mode is not programmed on as determined in step S112, then no ventricular pacing is triggered by a sensed non-refractory V-EVENT terminating the AV delay. The time-out of the TRIG_PACE window is commenced in step S113 simultaneously with the time-out of the V-A escape interval and post-event time periods in step S110.

If the V-A atrial escape interval is timed out by timer 370 in step S116 without a non-refractory A-EVENT being sensed across the selected pair of atrial sense electrodes, then the A-PACE pulse is delivered across the selected RA pace electrode pair in step S118, the AV delay is set to PAV in step S120, and the AV delay is commenced by AV delay timer 372.

If a non-refractory A-EVENT is generated as determined in steps S122 and S134, then the V-A escape interval is terminated. The ABP and ARP are commenced by post-event timers 374 in step S136, the AV delay is set to the SAV in step S138, and the SAV delay is started in step S100 and timed out by SAV/PAV delay timer 372.

Assuming that the normal activation sequence is sought to be restored, a programmed SAV and PAV delay corresponding to a normal AV conduction time from the AV node to the bundle of His are used or a calculated SAV and PAV delay is calculated in relation to the prevailing sensor rate or sensed intrinsic heart rate and are used by SAV/PAV delay timer 372.

Figure 7:
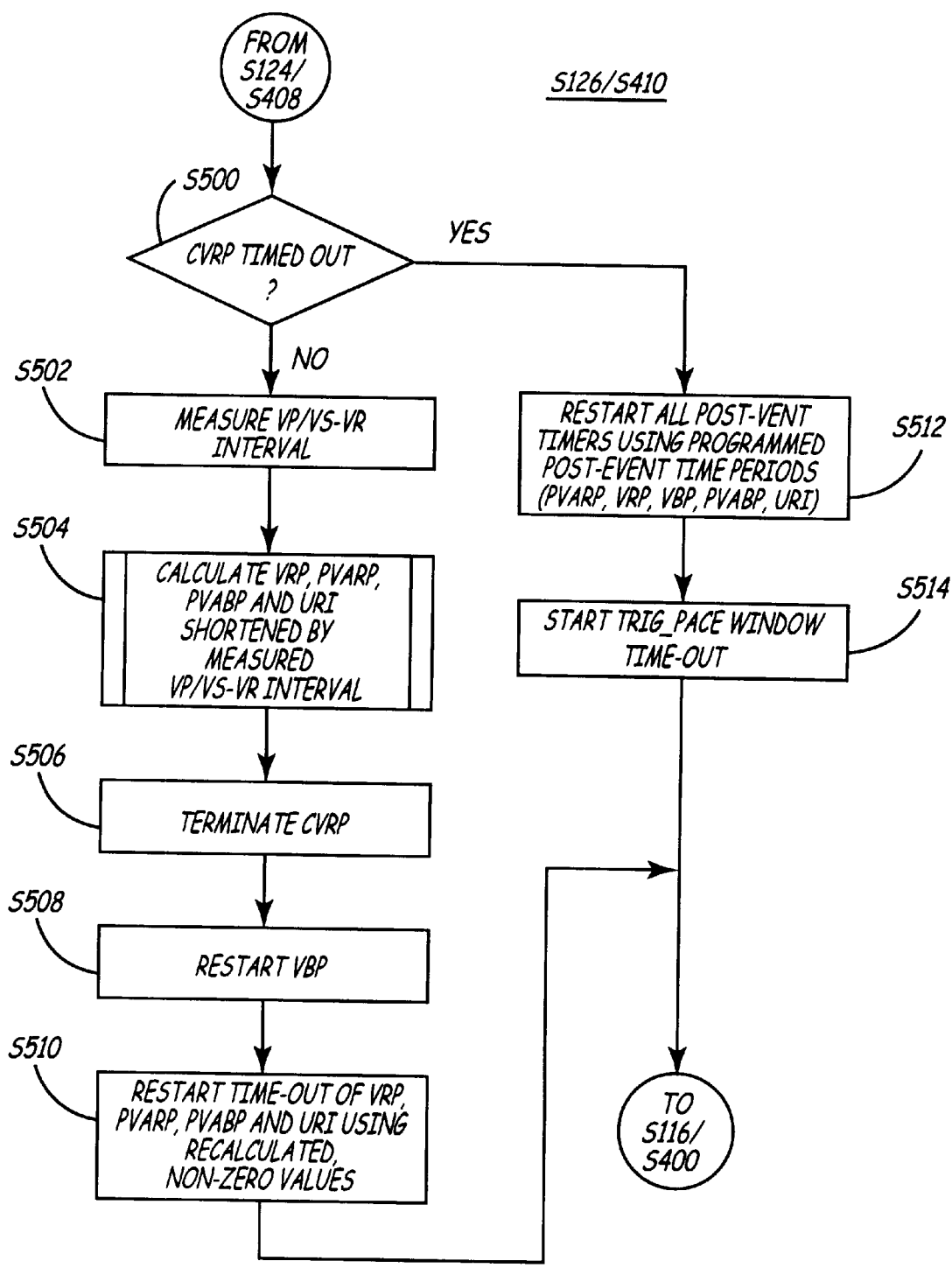
FIG. 7 is a flow chart illustrating the conditional ventricular refractory period (CVRP) response to the double sensing of a ventricular sense event during the time-out of a ventricular refractory period.

If an RV-EVENT or LV-EVENT or a collective V-EVENT sensed across the RV tip sense electrode and the LV sense electrode (for simplicity, all referred to as a V-EVENT) is detected in step S123 during the time-out of the V-A escape interval, then, it is determined if it is a non-refractory V-EVENT or a refractory V-EVENT in step S124. If the V-EVENT is determined to be a refractory V-EVENT in step S124, then it is employed in the CVRP processing step S126 (FIG. 7). If the V-EVENT is determined to be a non-refractory V-EVENT in step S124, then the V-A escape interval is restarted, and the post-ventricular time periods are restarted in step S128.

In step S130, it is determined whether a triggered pacing mode is programmed to be operative during the V-A escape interval. If one is programmed on, then it is undertaken and completed in step S132 (FIGS. 6A–6B). If triggered pacing is not programmed on as determined in step S130, then no ventricular pacing is triggered by the sensed non-refractory V-EVENT during the V-A escape interval. The time-out of the TRIG_PACE window is commenced in step S131 simultaneously with the time-out of the V-A escape interval and post-event time periods in step S128.

FIG. 5 depicts the step S106 in greater detail, and FIGS. 6A–6B depict the steps S114 and S132 in greater detail. As described in greater detail below, if a VP-VP pacing mode is programmed on in step S106, it can be selectively programmed in a left-to-right or right-to-left ventricle sequence, wherein the first and second delivered ventricular pacing pulses (V-PACE1 and V-PACE2) are separated by separately programmed VP-VP delays. If a bi-ventricular triggered pacing mode is programmed on in either or both of steps S114 and S132, it can be selectively programmed to immediately pace the ventricle from which the V-EVENT is sensed or a fixed or programmed ventricle regardless of where the V-EVENT is sensed with a V-PACE1. Then, the V-PACE2 is generated to synchronously pace the other ventricle after a programmed VSNP-VP delay. Or, the triggered pacing mode can be selectively programmed in either or both of steps S114 and 132 to only synchronously pace the other ventricle than the ventricle from which the V-EVENT is sensed with V-PACE2 after separately programmable VS-VP delays, depending on the right-to-left or left-to-right sequence. All of these VP-VP, VSNP-VP, and VS-VP delays are preferably programmable between approximately 0 and 80 msec.

As a practical matter, the minimum VS/VP-VP, and VP-VP delays may be set to one half the system clock cycle in order to avoid simultaneous delivery of RV-PACE and LV-PACE pulses. The pacing pulse width is typically programmable between about 0.5 msec and 2.0 msec, and the pacing pulse amplitude is typically programmable between 0.5 and 7.5 volts. The system clock provides a full clock cycle of about 8.0 msec. Therefore, the minimum VP-VP delay is set at a half clock cycle or about 4.0 msec.

As shown in FIG. 5, the IPG circuit 300 of FIG. 3 can be programmed to either only deliver a single RV-PACE or LV-PACE (V-PACE1) or the pair of RV-PACE and LV-PACE pulses (V-PACE1 and V-PACE2) separated by the VP-VP delay timed out by V-V delay timer 366. If delivery of only a single RV-PACE or LV-PACE is programmed as determined in step S200, then it is delivered in step S202. The pacing pulse is typically delivered across the active or cathode RV or LV tip electrodes 40 or 50 and one of the available indifferent electrodes that is programmed and selected through the pace electrode selection and control 350 depending upon which are present in the pacing system and the pacing vector that is desired. The indifferent electrodes depicted in FIG. 3 include the IND_RV electrode 38, the IND_CAN electrode 20, and the IND_LV electrode 58.

If VP-VP pacing is programmed on in step S200, then V-PACE1 is delivered in step S204 in the programmed RV-LV or LV-RV sequence. Again, the pacing pulse is typically delivered across the active, cathode RV or LV tip electrodes 40 or 50 and one of the available indifferent electrodes that is programmed and selected through the pace electrode selection and control 350 depending upon which are present in the pacing system and the pacing vector that is desired as set forth above. The V-PACE1 pacing pulse is delivered at a programmed pulse energy dictated by the programmed voltage and pulse width.

The V-V delay timer 366 is loaded with the programmed VP-VP delay and starts to time out in step S206. If the RV-PACE pulse is V-PACE1, then a programmed VP-VP delay is timed in V-V delay timer 366. The LV-PACE pulse is is delivered as V-PACE2 typically across the active LV pace electrode 50 and the programmed indifferent electrode in step S210 after time-out of the programmed VP-VP delay in step S208. Conversely, if the LV-PACE pulse is the first to be delivered (V-PACE1), then a programmed VP-VP delay is timed in V-V delay timer 366. The RV-PACE pulse is then delivered as V-PACE2 typically across the active RV pace electrode 40 and the programmed indifferent electrode in step S210 after time-out of the programmed VP-VP delay in step S208.

FIG. 6A–6B is a flow chart illustrating the steps S114 and S132 of FIG. 4 for delivering ventricular pacing pulses triggered by a ventricular sense event in step S108 during the time-out of an AV delay or in step S124 during time-out of the V-A escape interval. As noted above, the sensing of R-waves in the RV and LV can be accomplished employing several RV-SENSE and LV-SENSE sensing axes or vectors. A bipolar RV-SENSE vector (RV sense electrodes 38 and 40), a unipolar RV-SENSE vector (RV tip sense electrode 40 and IND_CAN electrode 20), and a unipolar LV-SENSE vector (LV sense electrode 50 and IND_CAN electrode 20), a bipolar LV-SENSE vector (LV sense electrodes 50 and 58), and a trans-ventricular, combined RV-SENSE and LV-SENSE vector (RV tip sense electrode 40 and LV sense electrode 50) can be programmed.

The IPG circuit 300 can be separately programmed in one of three triggered pacing modes designated VS/VP, VS/VP-VP or VS-VP triggered modes for each of steps S114 and S132. In the VSNP triggered pacing mode, a V-PACE1 is delivered without delay upon a RV-EVENT or LV-EVENT to the RV or LV pacing pathway, respectively. In the VS/VP-VP triggered pacing mode, the V-PACE1 is delivered without delay upon a RV-EVENT or LV-EVENT to the selected RV or LV pacing electrode pair, respectively, and a V-PACE2 is delivered to the other of the selected LV or RV pacing electrode pair after the VSNP-VP delay times out. In the VS-VP pacing mode, a RV-EVENT or the LV-EVENT starts time-out of a VS-VP delay, and a single pacing pulse (designated V-PACE2) is delivered to the selected LV or the RV pace electrode pair, respectively, when the VS-VP delay times out.

The TRIG_PACE time window started by a prior V-EVENT or V-PACE must have timed out in step S300 prior to delivery of any triggered ventricular pacing pulses. If it has not timed out, then triggered pacing cannot be delivered in response to a sensed V-EVENT. If the TRIG_PACE window has timed out, it is then restarted in step S302, and the programmed triggered pacing modes are checked in steps S304 and S316.

When IPG circuit 300 is programmed in the VS/VP-VP triggered mode as determined in step S304, the RV-EVENT or LV-EVENT triggers the immediate delivery of a respective RV-PACE or a LV-PACE or a programmed one of the RV-PACE or a LV-PACE across the programmed bipolar or unipolar RV and LV pace electrode pair, respectively, in step S306 as V-PACE1. Under certain circumstances, it is desirable to always deliver V-PACE1 to a designated RV or LV pace electrode pair, regardless of whether a RV-EVENT and LV-EVENT is sensed.

Then, a VS/VP-VP delay is started in step S308 and timed out in step S310. The VS/VP-VP delay is specified as a VP-VP delay when the RV-EVENT is sensed and the RV-PACE is V-PACE1 and the LV-PACE is V-PACE2. The VS/VP-VP delay is specified as a VP-VP delay when the LV-EVENT is sensed and the LV-PACE is V-PACE1 and the RV-PACE is V-PACE2. The LV-PACE or RV-PACE pulse is delivered at the programmed amplitude and pulse width across the programmed LV or RV pace electrode pair in step S210.

In step S314, it is determined whether the VS-VP triggered pacing mode or the VSNP triggered pacing mode is programmed. When the IPG circuit 300 is programmed to a VS/VP triggered pacing mode, the RV-EVENT or LV-EVENT triggers the immediate delivery of an RV-PACE or an LV-PACE across the programmed bipolar or unipolar RV or LV pace electrode pair, respectively, in step S316.

When the IPG circuit 300 is programmed to the VS-VP triggered pacing mode, an LV-EVENT as determined in step S318 loads the appropriate VS-VP delay in V-V delay timer 366 in step S320 and starts the VS-VP delay time-out in step S322. The RV-PACE is delivered at its time-out in step S322 (also designated V-PACE2). If an RV-EVENT is determined in step S318, then the appropriate VS-VP delay in V-V delay timer 366 in step S326 and the VS-VP delay is timed out in step S328. The LV-PACE (also designated V-PACE2) is delivered at time-out of the VS-VP delay in step S330.

The V-A escape interval is timed out in step SI 16 following the completion of the ventricular pacing mode of FIGS. 6A–6B for steps SI 14 and S132. If the V-A escape interval times out, then an RA pace pulse is typically first delivered across the RA pace electrodes 17 and 19 in step S118, and the AV delay timer is restarted in step S100.

It will be understood that other operations ancillary to the typical operation of an AV synchronous pacemaker or a pacemaker operating in single chamber pacing modes are conducted in the overall operation of a pacing system of this type, that are not necessary to the practice of the present invention. For example, it will be understood that recharge operations of the type described in the above-referenced Ser. No. 09/439,568 application can be conducted following the delivery of A-PACE and RV-PACE and LV-PACE pulses.

A number of post-ventricular time periods illustrated in the timing charts of FIGS. 8A–8D are timed out following V-PACE 1 in step S104 or the sensing of the V-EVENT in steps S110 and S128, including the CVRP. FIG. 7 is a flow chart illustrating the CVRP response to the double sensing of a ventricular sense event during the time-out of the CVRP. The invention illustrated in FIG. 7 avoids complications arising from double sensing of wide QRS complexes that can disrupt AV synchrony by unduly prolonging the post-ventricular time periods such that a legitimate A-EVENT is determined to be refractory in step S134 and is incapable of terminating the V-A escape interval and restarting the AV delay in step S100.

Figure 8A:
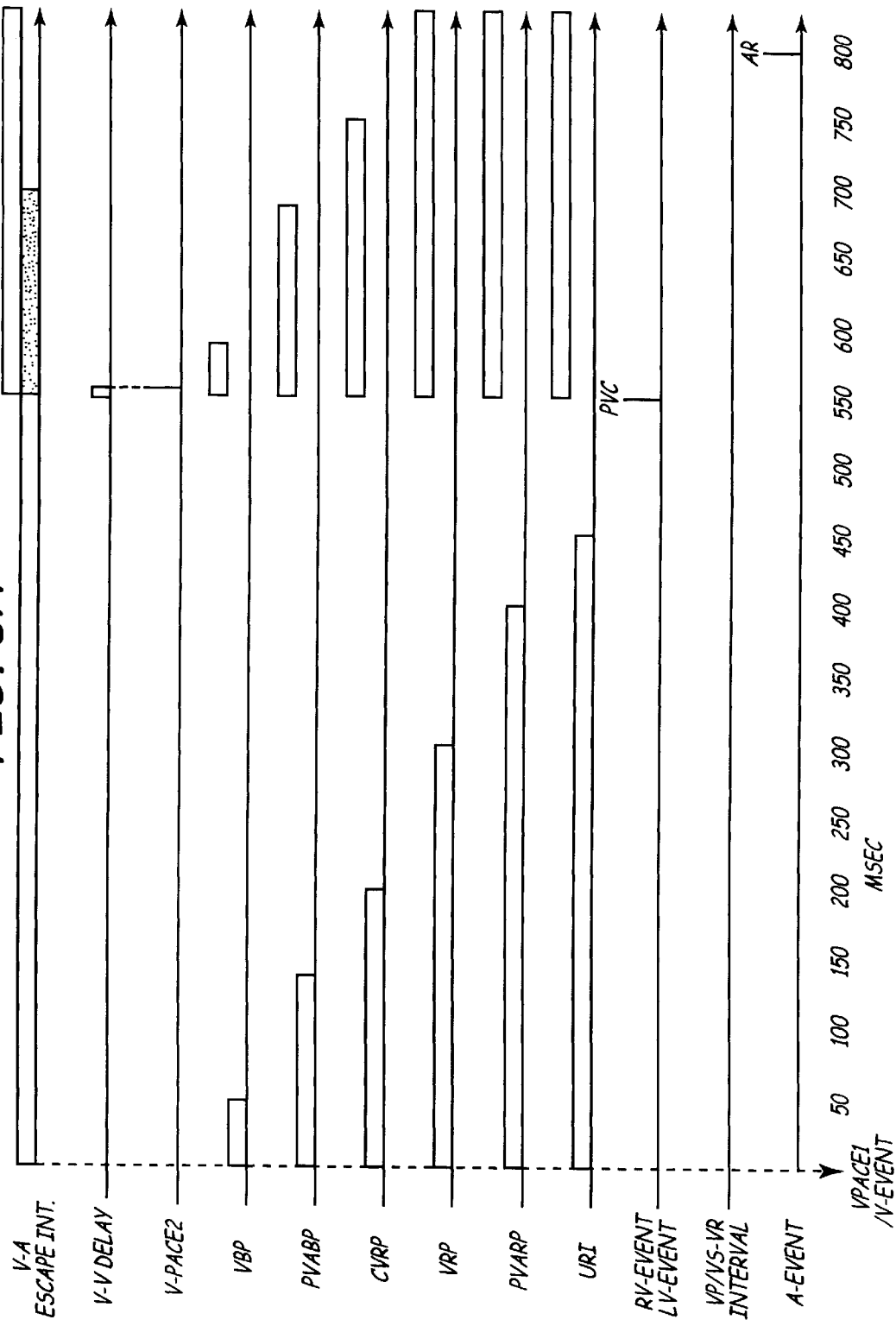
FIGS. 8A–8D are timing charts illustrating the starting and restarting of post-ventricular time periods by refractory ventricular sense events in accordance with the present invention following the operation of the algorithm of FIG. 7.

FIG. 8A illustrates the restarting of post-ventricular time periods by V-PACE1 or a V-EVENT. The 700 msec V-A escape interval is timed from the V-EVENT or V-PACE1. A V-EVENT occurs at 550 msec, and it may be characterized as a PVC since there is no intervening A-EVENT. The PVC follows the time-out of the VBP, PVABP, CVRP, VRP, PVARP and URI, and all of them are restarted. In addition, if a second pace is to be delivered, the appropriate V-V triggered pacing delay is started and V-PACE2 is again delivered at its time-out. If an A-EVENT occurs within the PVARP as indicated at 800 msec, it is ruled to be a refractory A-EVENT (designated an AR event). It cannot terminate the V-A escape interval and restart the AV delay.

Figure 8B:
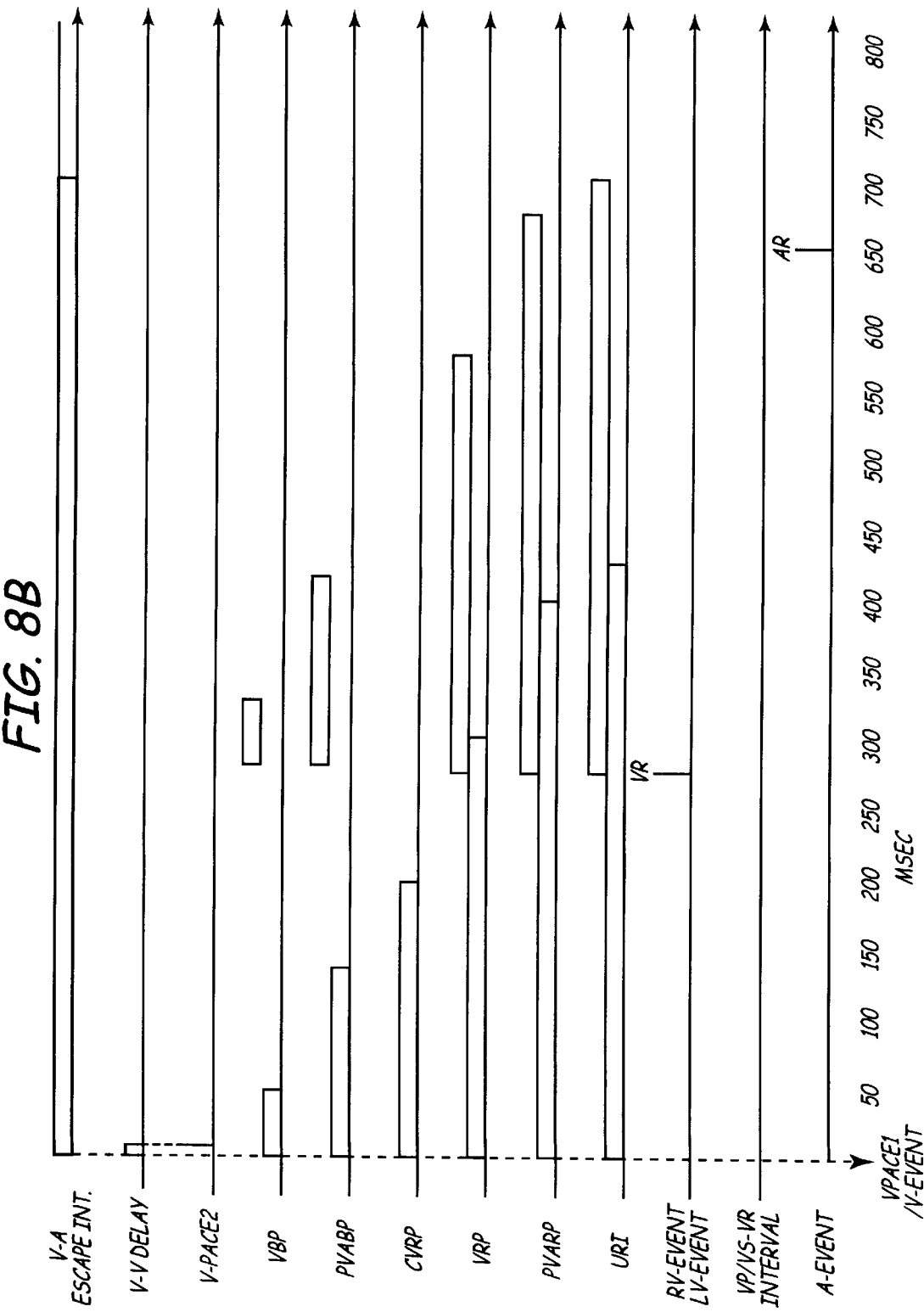

Similarly, if the V-EVENT occurs during the VRP as shown in FIG. 8B, it is a refractory V-EVENT designated a VR event. It causes the VBP, PVABP, VRP, PVARP, and URI to be restarted but does not terminate and restart the V-A escape interval or restart the CVRP. But, again, if an A-EVENT occurs within the PVARP as indicated at 650 msec, it is ruled to be an AR event. It cannot terminate the V-A escape interval and restart the AV delay.

If the V-EVENT triggering restarting of these post-ventricular time periods is a legitimate, but early, PVC or is noise mistakenly detected as a V-EVENT, then the restarting of the full post-ventricular time periods is appropriate. But, if the V-EVENT constitutes the detection of the trailing edge of a wide QRS, then this response illustrated in FIG. 8B is inappropriate and results in unnecessary loss of atrial synchrony. The CVRP comes into play to lessen the likelihood of this inappropriate response. It provides for the truncation of the restarted post-ventricular time periods in response to a single VR during the CVRP as shown in FIG. 8C but treats a second VR in the same manner as electrical noise as shown in FIG. 8D.

Returning to FIG. 7, a VR determined in step S124 of FIG. 4 triggers the determination of whether the CVRP has timed out in step S500. If it has timed out, then all of the post-ventricular timers are restarted in step S512 as shown in FIG. 8B and described above. The timing out of the TRIG_PACE window is restarted in step S514, and the V-A escape interval started in step S104 or S110 is timed out in step S116 of FIG. 4.

Figure 8C:
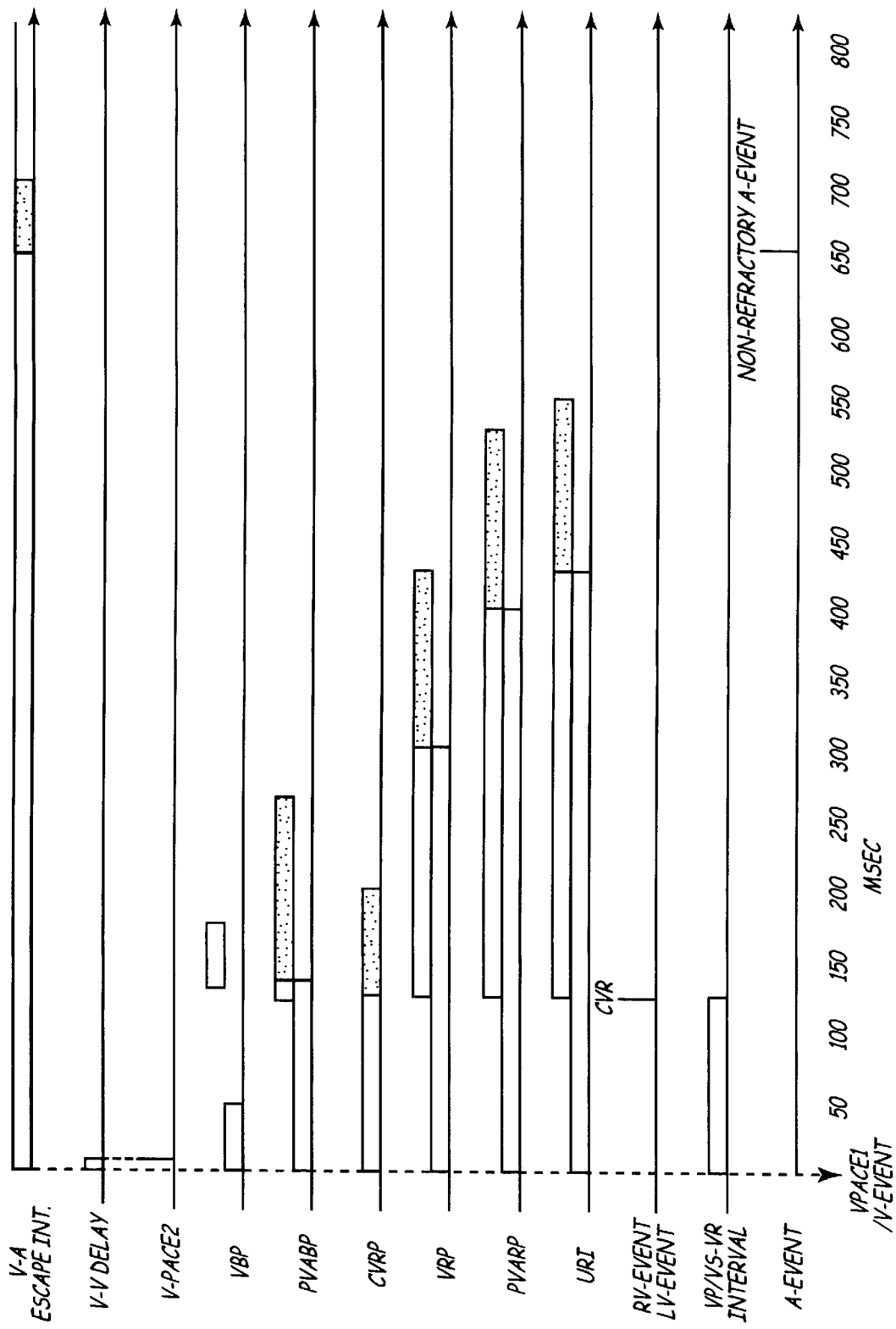

But, if the VR occurs before the CVRP has timed out (as shown in FIG. 8C where a VR designated a "CVR" occurs at 125 msec), then the VP/VS-VR time elapsed from the start of the CVRP to the VR is measured (in this case, 125 msec) in step S502. The VRP, PVARP, PVABP and URI are recalculated in step S504 by subtracting VP/VS-VR from the programmed VRP, PVARP, PVABP and URI, respectively. If any resulting time period is negative, then the recalculated period is set to "zero". Then, the CVRP is terminated in step S506 and the VBP is restarted in step S508. The VRP, It PVARP, PVABP and URI are restarted in step S510 as illustrated in FIG. 8C.

Figure 8D:
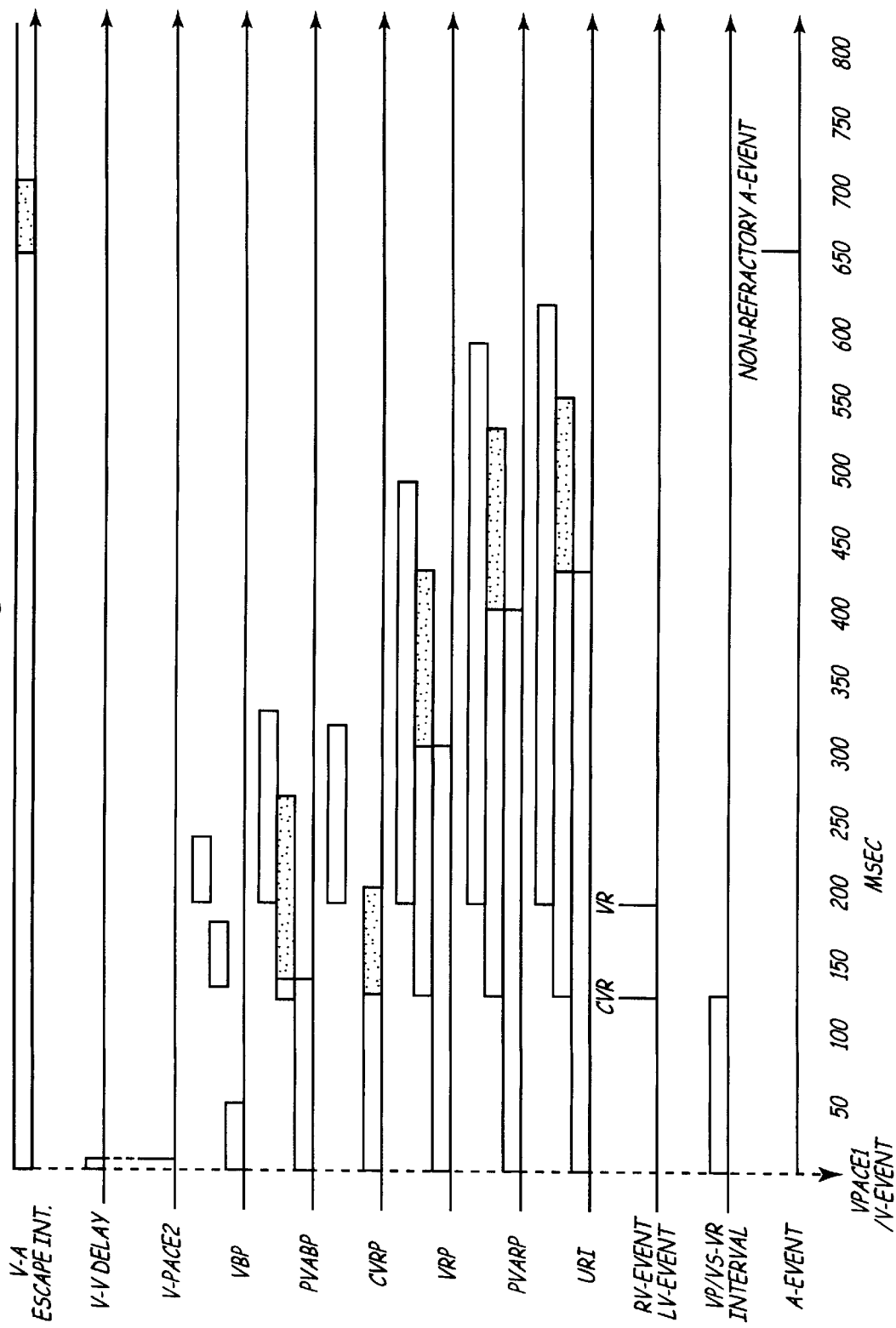

FIG. 8D shows a second, closely timed V-EVENT occurring after the VBP and during the time-out of the restarted post-ventricular time periods from the CVR but after the CVRP is terminated in step S506. The second V-EVENT and is then characterized as a VR event and noise reversion rules are invoked as shown in FIG. 8D. In this case, the V-EVENT is determined to be refractory in step S124 of FIG. 4, and steps S512 and S514 are followed as described above.

The present invention is implemented in a pacing system architecture wherein the post-event time periods, e.g. the PVARP and other time periods shown in FIGS. 8A–8D, are restarted, even those that have not expired as shown in FIGS. 8C and 8D when the CVR is provided. It will be understood that the equivalent approach of timing out the original post-event time periods that have not expired when the CVR occurs to their normal termination can also be undertaken.

These CVRP responses alleviate the problems that can arise from mistakenly sensing delayed conduction of the same spontaneous or evoked depolarization wave between right and left heart chambers. While they are described in the context of an AV synchronous, atrial synchronous pacemaker, they can be employed in a bi-atrial or bi-ventricular pacemaker.

The present invention may also be advantageously implemented in many of the bi-chamber pacing systems described above, e.g. those described in the above-incorporated '324 patent, or a single chamber pacemaker having two or more pace/sense electrodes located at spaced apart sites in the single heart chamber.

For example, FIG. 9 is a comprehensive flow-chart illustrating the operating modes of the IPG circuit 300 of FIG. 3 in a variety of multi-site, single chamber or bi-atrial or bi-ventricular pacing modes in accordance with a further embodiment of the invention selectively employing steps of FIGS. 5–7 therein. Thus, it will be assumed, for example, that the AV synchronous pacing DDD(R) mode is changed to an atrial or ventricular demand, and triggered pacing mode. When FIGS. 5–7 are incorporated into steps of FIG. 9 as described below, it will be understood that references to the ventricles (V) in those flow chart steps are appropriate to the bi-ventricular pacing system and method. However, references to the atria (A) can be substituted for the references to the ventricles (V) in those flow chart steps for an understanding of a bi-atrial pacing system and method.

Moreover, the references to "RV" and "LV" can be changed to "first site" and "second site" in the context of multi-site pacing at spaced apart sites in a single heart chamber where first and second pace/sense electrodes are located. It is contemplated that the multi-site pacing system can include further pace/sense electrodes at further spaced apart sites in excess of two sites and corresponding additional pacing pulse output amplifier circuits and/or sense amplifiers coupled by leads to such pace/sense electrodes. In such a case, the conditional refractory period (CRP) operations of the present invention described above in reference to FIGS. 8A–8D will be understood to be commenced upon a PACE1 delivered at time-out of an escape interval and/or upon the first EVENT generated by a sense amplifier coupled to any of the sites during the time-out of the escape interval and following the time-out of the TRIG_PACE window. For simplicity, the description of FIG. 9 is presented below in the context of a bi-chamber pacing system having pace/sense electrodes located at right and left heart chamber sites.

In step S400, the pacing escape interval started in step S418 from a prior R-EVENT or L-EVENT or previously delivered R-PACE or L-PACE event is timing out. If the escape interval times out, then in step S402 the TRIG-PACE window and the post-event time periods, including a conditional refractory period (CRP), the URI and the refractory period (RP) are commenced and timed out. At the same time, at least a PACE1 pacing pulse is delivered to one of the right or left heart chambers in step S404, and the pacing escape interval is restarted in step S418.

Step S404 is again depicted in FIG. 5 and operates as described above to either deliver a PACE1 to a selected right or left heart chamber or to deliver both PACE1 and PACE2 to both heart chambers in a programmed right-to-left or left-to right sequence separated by a programmed PACE-PACE trigger delay.

A R-EVENT or L-EVENT that is output by any of the right heart chamber (RHC) or left heart chamber (LHC) (or a trans-chamber sense amplifier), respectively, during the escape interval in step S402 is characterized as a refractory or non-refractory sense EVENT in step S406. If it is a refractory sense EVENT, then the CRP processing steps of FIG. 7 are followed as described above to determine if it falls within or follows the time-out of the CRP and by how much the post-event time periods are to be continued or extended. In this case, the post-event time periods do not include a PVARP or PVABP, and only include a blanking period (BP), refractory period (RP), and URI plus the CRP of the present invention.

Thus, the URI and the RP are either restarted as in FIG. 8B or restarted to time out to the same expiration time as the URI or RP being timed out as shown in FIG. 8C. The URI and RP are restarted for their full time periods if another refractory SENSE occurs during that time-out as shown in FIG. 8D. The escape interval being timed out is not restarted.

If a non-refractory SENSE occurs as depicted in FIG. 8A for example, then the CRP, the URI and the RP are commenced and timed out in step S412. At the same time, it is determined whether a triggered pacing mode is programmed on in step S414. If triggered pacing is off, then the escape interval is restarted in step S418. If a triggered pacing mode is on in step S414, then the steps of FIGS. 6A and 6B are followed in step S416, and the escape interval is restarted in step S418. In all cases, the starting of the escape interval in step S418 coincides with the starting of post-event timers in step S412, although it is shown as a later step in the flow chart.

In FIG. 6A, triggered pacing proceeds if programmed on in step S304 and if the non-refractory SENSE falls outside the TRIG_PACE window as determined In steps S300 and S302. If triggered pacing is programmed on, then it can be programmed to deliver PACE1 or PACE2 alone or both PACE1 and PACE2 in the manner prescribed in the remaining steps of FIG. 6A and 6B. The triggered pacing modes can include delivering PACE1 alone to the right or left heart chamber where the sense EVENT was provided or to a programmed one of the right or left heart chamber, regardless of where the depolarization was sensed per step S316.

Or, PACE 1 and PACE2, separated by the programmed or fixed PACE1–PACE2 delay, can be delivered per steps S306–S312 in a programmed sequence. The programmed sequence can comprise delivering PACE1 to the right or left heart chamber where the sense EVENT was provided or to a programmed one of the right or left heart chamber, regardless of where the depolarization was sensed, and then delivering PACE 2 to the other heart chamber at the time-out of the PACE1–PACE2 trigger delay.

Finally, delivery of PACE2 only can be programmed on, as determined in step S314. In that case, steps S314–S330 are followed as described above to deliver PACE2 to the other heart chamber than the heart chamber where the SENSE was provided by the sense amplifier coupled to it after time-out of a SENSE-PACE2 trigger delay.

The preceding specific embodiments are illustrative of the practice of the invention. It is to be understood, therefore, that other expedients known to those of skill in the art or disclosed herein may be employed.

It will be understood that certain of the above-described structures, functions and operations of the pacing systems of the preferred embodiments are not necessary to practice the present invention and are included in the description simply for completeness of an exemplary embodiment or embodiments. It will also be understood that there may be other structures, functions and operations ancillary to the typical operation of such pacing systems that are not disclosed and are not necessary to the practice of the present invention. In addition, it will be understood that specifically described structures, functions and operations set forth in the above-listed, commonly assigned and co-pending patent applications can be practiced in conjunction with the present invention, but they are not essential to its practice.

In the following claims, means-plus-function clauses are intended to cover the structures described herein as performing the recited function and not only structural equivalents but also equivalent structures. It is therefore to be understood, that within the scope of the appended claims, the invention may be practiced otherwise than as specifically described without actually departing from the spirit and scope of the present invention.

What is claimed is:

1. In an implantable medical device for cardiac pacing, a method of delivering triggered pacing pulses to the heart comprising the steps of:

locating first and second pace/sense electrodes at first and second spaced apart sites of the heart;

sensing spontaneous cardiac depolarizations traversing one of the other of the first and second pace/sense electrodes and providing a sense event signal;

upon provision of a sense event signal that is characterized as non-refractory, starting and timing out a pacing escape interval;

upon provision of a non-refractory sense event signal during the time-out of the pacing escape interval, terminating and restarting the pacing escape interval, and commencing and timing out a post-event time period adapted to be extended upon a sense event signal provided while it is being timed out and a conditional refractory period; and in response to provision of a sense event signal during the conditional refractory period, characterizing the sense event signal as a refractory sense event signal incapable of restarting the pacing escape interval, terminating the conditional refractory period, and timing out the remaining period of the post-event time period without extending it, whereby the undue prolongation of the post-event period due to a sense event resulting from sensing of delayed propagation of a single heart chamber depolarization between the first and second pace/sense electrodes is avoided and legitimate right or left heart chamber sense event signals occurring thereafter are not characterized as refractory and are able to restart the pacing escape interval.

2. In an implantable medical device for cardiac pacing, a cardiac pacemaker for delivering first and second pacing pulses to the heart comprising:

lead means for locating first and second pace/sense electrodes at first and second spaced apart sites of the heart;

sensing means for sensing spontaneous cardiac depolarizations traversing one or the other of the first and second pace/sense electrodes and providing a sense event signal;

an escape interval timer operable upon provision of a sense event signal that is characterized as non-refractory for starting and timing out pacing escape interval;

means operable upon provision of a non-refractory sense event signal during the time-out of the pacing escape interval for terminating and restarting the pacing escape interval and for commencing and timing out a post-event time period adapted to be extended upon a sense event signal provided while it is being timed out and a conditional refractory period; and means responsive to provision of a sense event signal during the conditional refractory period for characterizing the sense event signal as a refractory sense event signal incapable of restarting the pacing escape interval, terminating the conditional refractory period, and timing out the remaining period of the post-event time period without extending it, whereby the undue prolongation of the post-event period due to a sense event resulting from sensing of delayed propagation of a single heart chamber depolarization between the first and second pace/sense electrodes is avoided and legitimate right or left heart chamber sense event signals occurring thereafter are not characterized as refractory and are able to restart the pacing escape interval.

3. In an implantable medical device for cardiac pacing, a method of sensing spontaneous cardiac depolarizations in right and left heart chambers and selectively delivering right and left heart chamber pacing pulses to the right and left heart chambers for improving the hemodynamic efficiency of a sick heart suffering from conduction delays in conducting spontaneous or evoked depolarizations through the right and left heart chambers that compromise cardiac output, wherein said method comprises the steps of:

sensing spontaneous cardiac depolarizations in the right heart chamber and providing right heart chamber sense event signals;

sensing spontaneous cardiac depolarizations in the left heart chamber and providing left heart chamber sense event signals;

timing out a pacing escape interval establishing a pacing rate from a selected one of the right and left heart chamber sense event signals that is characterized as non-refractory;

upon provision of a non-refractory right heart chamber or left heart chamber sense event signal during the time-out of the pacing escape interval, terminating and restarting the pacing escape interval, and commencing and timing out a post-event time period adapted to be extended upon a sense event signal provided while it is being timed out and a conditional refractory period; and in response to provision of a right or left heart chamber sense event signal during the conditional refractory period, characterizing the sense event signal as a refractory sense event signal incapable of restarting the pacing escape interval, terminating the conditional refractory period, and timing out the remaining period of the post-event time period without extending it, whereby the undue prolongation of the post-event period due to a sense event resulting from sensing of delayed propagation of a single heart chamber depolarization between the left and right heart chambers is avoided and legitimate right or left heart chamber sense event signals occurring thereafter are not characterized as refractory and are able to restart the pacing escape interval.

4. The method of claim 3, wherein the post-event time period is a refractory period exceeding the conditional refractory period and further comprising the step of:

characterizing a right or left heart chamber sense event occurring during the refractory period as a refractory sense event signal incapable of restarting the pacing escape interval.

5. The method of claim 4, wherein the step of timing out the refractory period extended in response to a refractory sense event occurring during the conditional refractory period further comprises the steps of:

calculating the elapsed time between the starting and termination of the conditional refractory period;

shortening the refractory period by the calculated elapsed time; and restarting the refractory period.

6. The method of claim 3, wherein the step of timing out the post-event time period extended in response to a refractory sense event occurring during the conditional refractory period further comprises the steps of:

calculating the elapsed time between the starting and termination of the conditional refractory period;

shortening the post-event time period by the calculated elapsed time; and restarting the post-event time period.

7. The method of claim 3, further comprising the steps of:

at the time-out of the pacing escape interval, delivering a first pacing pulse either as a right heart chamber pacing pulse to the right heart chamber to evoke a right heart chamber depolarization or as a left heart chamber pacing pulse to the left heart chamber to evoke a left heart chamber depolarization; and upon delivery of the first pacing pulse, restarting the timing out of the pacing escape interval and commencing and timing out the post-event time period adapted to be extended upon a sense event signal provided while it is being timed out and the conditional refractory period.

8. The method of claim 7, further comprising the steps of:

at the time-out of the pacing escape interval, commencing and timing out a triggered pacing delay; and at the time-out of the triggered pacing delay, delivering a pacing pulse to the other of the left heart chamber or the right heart chamber to evoke a synchronized depolarization of the right and left heart chambers.

9. The method of claim 3, further comprising the step of:

upon provision of a non-refractory right heart chamber or left heart chamber sense event signal, delivering a pacing pulse to a predetermined one of the right heart chamber or the left heart chamber.

10. The method of claim 3, further comprising the steps of:

upon provision of a non-refractory right heart chamber or left heart chamber sense event signal, commencing and timing out a triggered pacing delay; and at the time-out of the triggered pacing delay, delivering a pacing pulse to the other of the left heart chamber or the right heart chamber to evoke a synchronized depolarization of the right and left heart chambers.

11. The method of claim 3, further comprising the steps of:

upon provision of a non-refractory right heart chamber or left heart chamber sense event signal, commencing and timing out a triggered pacing delay and delivering a first pacing pulse to one of the right heart chamber or the left heart chamber; and at the time-out of the triggered pacing delay, delivering a second pacing pulse to the other of the left heart chamber or the right heart chamber to evoke a synchronized depolarization of the right and left heart chambers.

12. In an implantable medical device for cardiac pacing, a cardiac pacemaker of the type providing sensing of spontaneous cardiac depolarizations in right and left heart chambers and selectively delivering right and left heart chamber pacing pulses to the right and left heart chambers for improving the hemodynamic efficiency of a sick heart suffering from conduction delays in conducting spontaneous or evoked depolarizations through the right and left heart chambers that compromise cardiac output, wherein said pacemaker comprises:

a left heart chamber pace/sense lead adapted to be advanced into a left heart chamber blood vessel to situate a left heart chamber pace/sense electrode adjacent to the left heart chamber;

a right heart chamber pace/sense lead adapted to be advanced into the right heart chamber to locate a right heart chamber pace/sense electrode in relation to the right heart chamber; and a pacing pulse generator comprising:

a right heart sense amplifier coupled to said right heart chamber pace/sense electrode for sensing spontaneous cardiac depolarizations in the right heart chamber and providing right heart chamber sense event signals;

a left heart chamber sense amplifier coupled to said left heart chamber pace/sense electrode for sensing spontaneous cardiac depolarizations in the left heart chamber and providing left heart chamber sense event signals;

an escape interval timer for timing out a pacing escape interval establishing a pacing rate from a selected one of the right and left heart chamber sense event signals that is characterized as non-refractory;

means responsive to provision of a non-refractory right heart chamber or left heart chamber sense event signal for terminating and restarting the pacing escape interval, commencing and timing out a post-event time period adapted to be extended upon a sense event signal provided while it is being timed out, and the conditional refractory period; and means operable in response to provision of a right or left heart chamber sense event signal during the conditional refractory period for characterizing the sense event signal as a refractory sense event signal incapable of restarting the pacing escape interval, for terminating the conditional refractory period, and for timing out the remaining period of the post-event time period without extending it, whereby the undue prolongation of the post-event period due to a sense event resulting from sensing of delayed propagation of a single heart chamber depolarization between the left and right heart chambers is avoided and legitimate right or left heart chamber sense event signals occurring thereafter are not characterized as refractory and are able to restart the pacing escape interval.

13. The pacemaker of claim 12, wherein the post-event time period is a refractory period exceeding the conditional refractory period and further comprising:

means for characterizing a right or left heart chamber sense event occurring during the refractory period as a refractory sense event signal incapable of restarting the pacing escape interval.

14. The pacemaker of claim 13, wherein the means for timing out the refractory period extended in response to a refractory sense event occurring during the conditional refractory period further comprises:

means for calculating the elapsed time between the starting and termination of the conditional refractory period;

means for shortening the refractory period by the calculated elapsed time; and means for restarting the refractory period.

15. The pacemaker of claim 12, wherein the means for timing the post-event time period extended in response to a refractory sense event occurring during the conditional refractory period further comprises:

means for calculating the elapsed time between the starting and termination of the conditional refractory period;

means for shortening the post-event time period by the calculated elapsed time; and means for restarting the post-event time period.

16. The pacemaker of claim 12, further comprising:

first pacing pulse generating means operable at the time-out of the pacing escape interval for delivering a first pacing pulse either as a right heart chamber pacing pulse to the right heart chamber pace/sense electrode to evoke a right heart chamber depolarization or as a left heart chamber pacing pulse to the left heart chamber pace/sense electrode to evoke a left heart chamber depolarization; and means operable upon delivery of the first pacing pulse for restarting the timing out of the pacing escape interval and for commencing and timing out a post-event time period adapted to be extended upon a sense event signal provided while it is timed out and the conditional refractory period.

17. The pacemaker of claim 16, further comprising:
means operable upon time-out of the pacing escape interval for commencing and timing out a triggered pacing delay; and
second pacing pulse generating means operable at the time-out of the triggered pacing delay for delivering a second pacing pulse to the other of the left heart chamber or the right heart chamber pace/sense electrode to evoke a synchronized depolarization of the right and left heart chambers.

18. The pacemaker of claim 12, further comprising:
means responsive to provision of a non-refractory right heart chamber or left heart chamber sense event signal for commencing and timing out a triggered pacing delay; and
pacing pulse generating means operable at the time-out of the triggered pacing delay, delivering a pacing pulse to the other of the left heart chamber pace/sense electrode or the right heart chamber pace/sense electrode to evoke a synchronized depolarization of the right and left heart chambers.

19. The pacemaker of claim 12, further comprising:
means responsive to provision of a non-refractory right heart chamber or left heart chamber sense event signal for commencing and timing out a triggered pacing delay;
first pacing pulse generating means operable upon provision of a non-refractory right heart chamber or left heart chamber sense event signal for generating and delivering a first pacing pulse to one of the right heart chamber pace/sense electrode or the left heart chamber pace/sense electrode; and
second pacing pulse generating means operable at the time-out of the triggered pacing delay for delivering a second pacing pulse to the other of the left heart chamber pace/sense electrode or the right heart chamber pace/sense electrode to evoke a synchronized depolarization of the right and left heart chambers.

20. The pacemaker of claim 12, further comprising:
means responsive to provision of a non-refractory right heart chamber or left heart chamber sense event signal for delivering a pacing pulse to a predetermined one of the right heart chamber pace/sense electrode or the left heart chamber pace/sense electrode.

21. In an implantable medical device for cardiac pacing at multiple sites, a method of selectively sensing spontaneous cardiac depolarizations in the right and left ventricles and delivering pacing pulses to the right and left heart ventricles for improving the hemodynamic efficiency of a sick heart suffering from conduction delays in conducting spontaneous or evoked depolarizations through the right and left ventricles that compromise cardiac output, wherein said method comprises the steps of:
sensing spontaneous atrial depolarizations and providing atrial sense event signals;
characterizing ones of the atrial sense event signals as non-refractory;
timing out an AV delay from the atrial sense event signals that are characterized as non-refractory;
sensing spontaneous cardiac depolarizations in the right ventricle and providing right ventricular sense event signals;
sensing spontaneous cardiac depolarizations in the left ventricle and providing left ventricular sense event signals;
timing out a V-A escape interval establishing a pacing rate from a selected one of the right and left ventricular sense event signals occurring during the AV delay or the V-A escape interval that is characterized as non-refractory;
upon provision of a non-refractory right ventricular or left ventricular sense event signal during the time-out of the V-A escape interval, terminating and restarting the V-A escape interval, and commencing and timing out a post-event time period adapted to be extended upon a ventricular sense event signal provided while it is being timed out and a conditional ventricular refractory period; and
in response to provision of a right or left ventricular sense event signal during the conditional ventricular refractory period, characterizing the ventricular sense event signal as a refractory ventricular sense event signal incapable of restarting the V-A escape interval, terminating the conditional ventricular refractory period, and timing out the remaining period of the post-event time period without extending it,
whereby the undue prolongation of the post-event period due to a ventricular event sense event resulting from sensing of delayed propagation of a single ventricular depolarization between the left and right ventricles is avoided and legitimate atrial sense event signals occurring thereafter are not characterized as refractory and are able to restart the AV delay.

22. The method of claim 21, wherein the post-event time period is a post-ventricular atrial refractory period exceeding the conditional ventricular refractory period and further comprising the step of:
characterizing an atrial sense event occurring during the post-ventricular atrial refractory period as a refractory atrial sense event signal incapable of restarting the AV delay.

23. The method of claim 22, wherein the step of timing out the post-ventricular atrial refractory time period extended in response to a refractory ventricular sense event occurring during the conditional ventricular refractory period further comprises the steps of:
calculating the elapsed time between the starting and termination of the conditional ventricular refractory period;
shortening the post-ventricular atrial refractory period by the calculated elapsed time; and
restarting the post-ventricular atrial refractory period.

24. The method of claim 22, wherein the step of timing out the post-event time period extended in response to a refractory ventricular sense event occurring during the conditional ventricular refractory period further comprises the steps of:
calculating the elapsed time between the starting and termination of the conditional ventricular refractory period;
shortening the post-event time period by the calculated elapsed time; and
restarting the post-event time period.

25. The method of claim 22, further comprising the steps of:
at the time-out of the AV delay, delivering a first pacing pulse either as a right ventricular pacing pulse to the right ventricle to evoke a right ventricular depolarization or as a left ventricular pacing pulse to the left ventricle to evoke a left ventricular depolarization; and upon delivery of the first pacing pulse, restarting the timing out of the V-A escape interval and commencing and timing out a post-event time period adapted to be extended upon a ventricular sense event signal provided while it is timed out and a conditional ventricular refractory period.

26. The method of claim 25, further comprising the steps of:

at the time-out of the AV delay, commencing and timing out a triggered pacing delay; and at the time-out of the triggered pacing delay, delivering a pacing pulse to the other of the left ventricle or the right ventricle to evoke a synchronized depolarization of the right and left heart chambers.

27. The method of claim 22, further comprising the steps of:

upon provision of a non-refractory right ventricular or left ventricular sense event signal, commencing and timing out a triggered pacing delay; and at the time-out of the triggered pacing delay, delivering a pacing pulse to the other of the left ventricular or the right ventricular to evoke a synchronized depolarization of the right and left ventricles.

28. The method of claim 22, further comprising the steps of:

upon provision of a non-refractory right ventricular or left ventricular sense event signal, commencing and timing out a triggered pacing delay and delivering a first pacing pulse to one of the right ventricle or the left ventricle; and at the time-out of the triggered pacing delay, delivering a second pacing pulse to the other of the left ventricle or the right ventricle to evoke a synchronized depolarization of the right and left ventricles.

29. The method of claim 22, further comprising the step of:

upon provision of a non-refractory right ventricular or left ventricular sense event signal, delivering a pacing pulse to a predetermined one of the right ventricles or the left ventricles.

30. In an implantable medical device for cardiac pacing at multiple sites, a system for selectively sensing spontaneous cardiac depolarizations in the right and left ventricles and delivering pacing pulses to the right and left heart ventricles for improving the hemodynamic efficiency of a sick heart suffering from conduction delays in conducting spontaneous or evoked depolarizations through the right and left ventricles that compromise cardiac output, wherein said pacemaker further comprises:

an atrial pace/sense lead adapted to be advanced into relation with an atrial chamber to situate an atrial pace/sense electrode adjacent to the atrial chamber;

ventricular pace/sense lead means for situating a first ventricular pace/sense electrode at a first ventricular site and a second ventricular pace/sense electrode at a second ventricular site spaced from said first ventricular site; and a pacing pulse generator coupled to said atrial pace/sense lead and said ventricular pace/sense lead means comprising:

an atrial sense amplifier coupled to said atrial pace/sense electrode for sensing spontaneous atrial depolarizations and providing atrial sense event signals;

means for characterizing ones of the atrial sense event signals as non-refractory;

an AV delay timer for timing out an AV delay from the atrial sense event signals that are characterized as non-refractory;

a right ventricular sense amplifier coupled to said right ventricular pace/sense electrode for sensing spontaneous cardiac depolarizations in the right ventricle and providing right ventricular sense event signals;

a left ventricular sense amplifier coupled to said left ventricular electrode for sensing spontaneous cardiac depolarizations in the left ventricle and providing left ventricular sense event signals;

an escape interval timer for timing out a V-A escape interval establishing a pacing rate from a selected one of the right and left ventricular sense event signals occurring during the AV delay or the V-A escape interval that is characterized as non-refractory; and means operable in response to provision of a right or left ventricular sense event signal during the conditional ventricular refractory period for characterizing the ventricular sense event signal as a refractory ventricular sense event signal incapable of restarting the V-A escape interval, for terminating the conditional ventricular refractory period, and for timing out the remaining period of the post-event time period without extending it, whereby the undue prolongation of the post-event period due to a ventricular event sense event resulting from sensing of delayed propagation of a single ventricular depolarization between the left and right ventricles is avoided and legitimate atrial sense event signals occurring thereafter are not characterized as refractory and are able to restart the AV delay.

31. The pacemaker of claim 30, further comprising:

a trigger pace timer operable upon provision of a non-refractory right ventricular or left ventricular sense event signal for commencing and timing out a triggered pacing delay; and pacing pulse generating means operable at the time-out of the triggered pacing delay for delivering a pacing pulse to the other of the left ventricular or the right ventricular to evoke a synchronized depolarization of the right and left ventricles.

32. The pacemaker of claim 30, wherein the post-event time period is a post-ventricular atrial refractory period exceeding the conditional ventricular refractory period and further comprising:

means for characterizing an atrial sense event occurring during the post-ventricular atrial refractory period as a refractory atrial sense event signal incapable of restarting the AV delay.

33. The pacemaker of claim 32, wherein the means for timing out the post-ventricular atrial refractory time period extended in response to a refractory ventricular sense event occurring during the conditional ventricular refractory period further comprises:

means for calculating the elapsed time between the starting and termination of the conditional ventricular refractory period;

means for shortening the post-ventricular atrial refractory period by the calculated elapsed time; and means for restarting the post-ventricular atrial refractory period.

34. The pacemaker of claim 30, wherein the means for timing out the post-event time pepnod extended in response to a refractory ventricular sense event occurring during the conditional ventricular refractory period further comprises:

means for calculating the elapsed time between the starting and termination of the conditional ventricular refractory period;

means for shortening the post-event time period by the calculated elapsed time; and means for restarting the post-event time period.

35. The pacemaker of claim 30, further comprising:

first pacing pulse generating means operable at the time-out of the AV delay for delivering a first pacing pulse either as a right ventricular pacing pulse to the right ventricular pace/sense electrode to evoke a right ventricular depolarization or as a left ventricular pacing pulse to the left ventricular pace/sense electrode to evoke a left ventricular depolarization; and means operable upon delivery of the first pacing pulse for restarting the timing out of the V-A escape interval and commencing and timing out a post-event time period adapted to be extended upon a ventricular sense event signal provided while it is timed out and a conditional ventricular refractory period.

36. The pacemaker of claim 35, further comprising:

a trigger pace timer operable at the time-out of the AV delay for commencing and timing out a triggered pacing delay; and second pacing pulse generating means operable at the time-out of the triggered pacing delay for delivering a pacing pulse to the other of the left ventricle or the right ventricle to evoke a synchronized depolarization of the right and left ventricles.

37. The pacemaker of claim 30, further comprising:

pacing pulse generating means operable upon provision of a non-refractory right ventricular or left ventricular sense event signal for delivering a pacing pulse to a predetermined one of the right ventricles or the left ventricles.

38. The pacemaker of claim 30, further comprising:

a trigger pace timer operable upon provision of a non-refractory right ventricular or left ventricular sense event signal for commencing and timing out a triggered pacing delay;

first, pacing pulse generating means operable upon provision of a non-refractory right ventricular or left ventricular sense event signal for delivering a first pacing pulse to one of the right ventricular pace/sense electrode or the left ventricular pace/sense electrode; and second pacing pulse generating means operable at the time-out of the triggered pacing delay for delivering a second pacing pulse to the other of the left ventricular pace/sense electrode or the right ventricular pace/sense electrode to evoke a synchronized depolarization of the right and left ventricles.

* * * * *

UNITED STATES PATENT AND TRADEMARK OFFICE
CERTIFICATE OF CORRECTION

PATENT NO.  : 6,496,730 B1  Page 1 of 1
DATED       : December 17, 2003
INVENTOR(S) : Charles G. Yerich et al.

It is certified that error appears in the above-identified patent and that said Letters Patent is hereby corrected as shown below:

Column 28,
Line 67, "time pepnod" should read -- time period --

Column 30,
Line 16, "first, pacing" should read -- first pacing --

Signed and Sealed this

Eighteenth Day of May, 2004

JON W. DUDAS
*Acting Director of the United States Patent and Trademark Office*